(12) United States Patent
Kusters

(10) Patent No.: US 12,138,640 B2
(45) Date of Patent: Nov. 12, 2024

(54) SYSTEMS AND METHODS FOR PRIMING A CONTINUOUS-FLOW CENTRIFUGE CHAMBER

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 541 days.

(21) Appl. No.: 17/527,340

(22) Filed: Nov. 16, 2021

(65) Prior Publication Data

US 2022/0152630 A1 May 19, 2022

Related U.S. Application Data

(60) Provisional application No. 63/115,368, filed on Nov. 18, 2020.

(51) Int. Cl.
*B04B 9/10* (2006.01)
*B04B 5/04* (2006.01)
*B04B 11/02* (2006.01)

(52) U.S. Cl.
CPC .............. *B04B 9/10* (2013.01); *B04B 5/0442* (2013.01); *B04B 11/02* (2013.01)

(58) Field of Classification Search
CPC ......... B04B 9/10; B04B 5/0442; B04B 11/02; A61M 1/36222; A61M 1/362227; A61M 1/36225; A61M 1/3696; A61M 1/3644; A61M 2205/331; A61M 2205/3365
See application file for complete search history.

(56) References Cited

U.S. PATENT DOCUMENTS

| | | |
|---|---|---|
| 5,194,145 A | 3/1993 | Schoendorfer |
| 5,316,667 A | 5/1994 | Brown et al. |
| 5,632,893 A | 5/1997 | Brown et al. |
| 5,868,696 A | 2/1999 | Giesler et al. |
| 6,419,822 B2 | 7/2002 | Muller et al. |
| 8,075,468 B2 | 12/2011 | Min et al. |
| 8,556,793 B2 | 10/2013 | Foley et al. |
| 2003/0195455 A1 | 10/2003 | Bainbridge et al. |
| 2019/0369008 A1 | 12/2019 | Kusters |

FOREIGN PATENT DOCUMENTS

WO WO2018/053217 A1 3/2018

OTHER PUBLICATIONS

Extended European Search Report, dated Apr. 4, 2022, for application No. EP21208371.1-1113.

*Primary Examiner* — Walter D. Griffin
*Assistant Examiner* — Shuyi S. Liu
(74) *Attorney, Agent, or Firm* — Cook Alex Ltd.

(57) ABSTRACT

A fluid processing device includes a controller, a centrifuge configured to receive and rotate a continuous-flow centrifuge chamber, a pump system, an optical detection assembly, and a pressure sensor. The controller executes a priming procedure in which a priming fluid is conveyed into the centrifuge chamber while the chamber is being rotated by the centrifuge, which moves air out of the chamber via a low-g outlet conduit. Upon detecting priming fluid exiting the centrifuge chamber via the low-g outlet conduit, the chamber is rotated at a higher rate to attempt to move any remaining air out of the chamber via the low-g outlet conduit. The controller then determines, based on signals from the optical detection assembly and pressure sensor, whether there is any air remaining in the centrifuge chamber. If so, the rotational rate is alternately decreased and increased until all the air has been cleared from the centrifuge chamber.

20 Claims, 14 Drawing Sheets

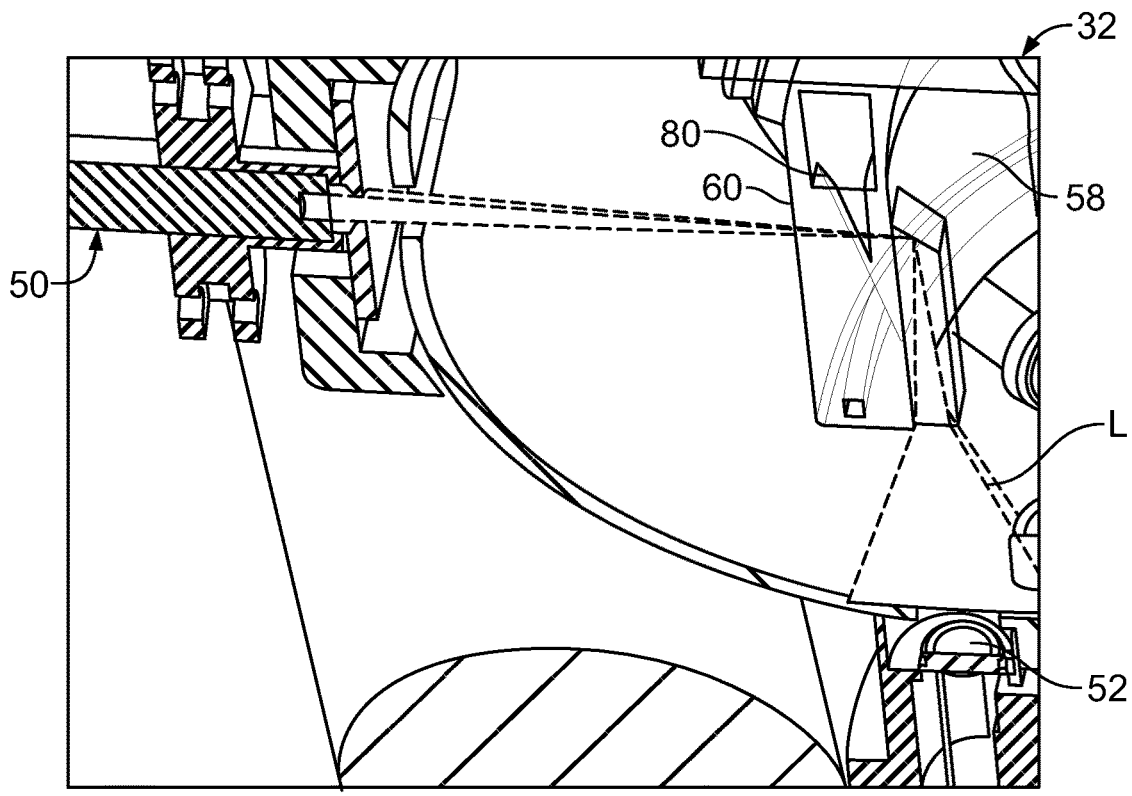
FIG. 7
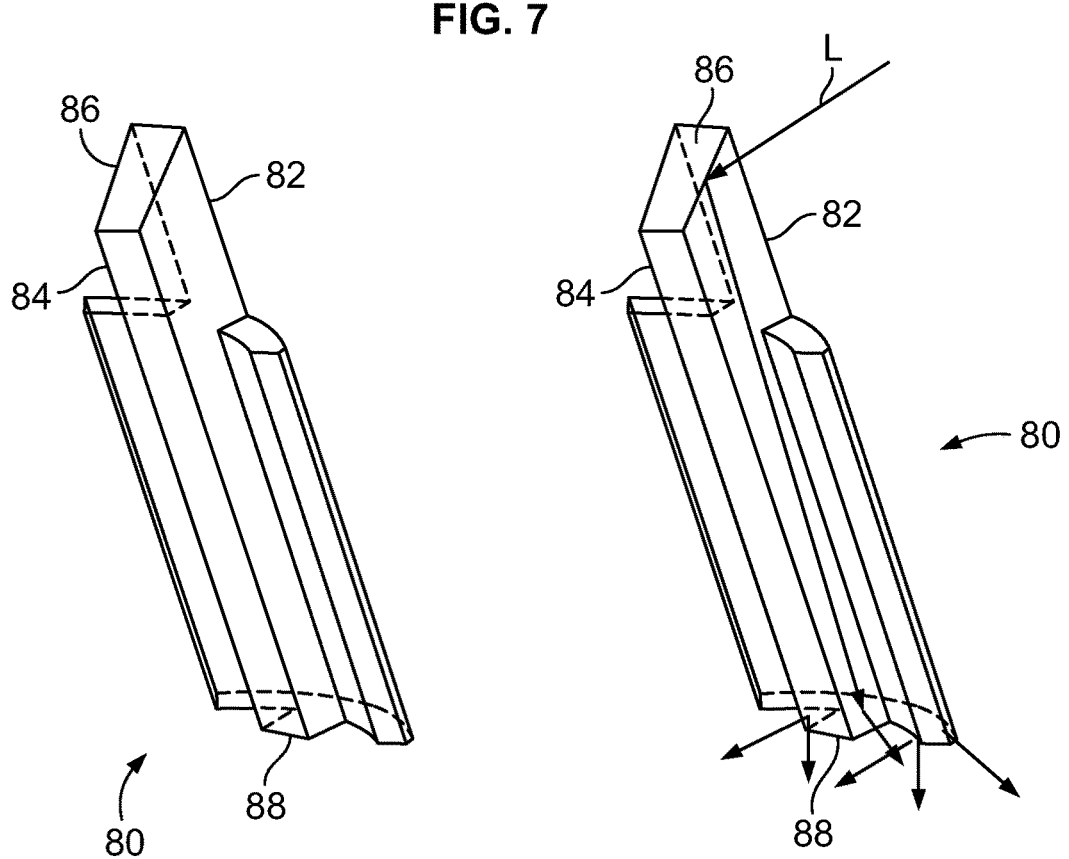
FIG. 14
FIG. 15

SYSTEMS AND METHODS FOR PRIMING A CONTINUOUS-FLOW CENTRIFUGE CHAMBER

CROSS-REFERENCE TO RELATED APPLICATIONS

This application claims the benefit of and priority of U.S. Provisional Patent Application Ser. No. 63/115,368, filed Nov. 18, 2020, the contents of which are incorporated by reference herein.

BACKGROUND

Field of the Disclosure

The present disclosure relates to continuous-flow centrifuges. More particularly, the present disclosure relates to priming a continuous-flow centrifuge chamber.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow circuit during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid flow circuit that is mounted in cooperation on the hardware. The centrifuge assembly engages and spins a disposable centrifuge chamber of the fluid flow circuit during a collection procedure. The blood, however, makes actual contact only with the fluid flow circuit, which assembly is used only once and then discarded.

As the whole blood is spun by the centrifuge, the heavier (greater specific gravity) components, such as red blood cells, move radially outwardly away from the center of rotation toward the outer or "high-g" wall of the separation chamber. The lighter (lower specific gravity) components, such as plasma, migrate toward the inner or "low-g" wall of the separation chamber. Various ones of these components can be selectively removed from the whole blood by forming appropriately located channeling seals and outlet ports in the separation chamber.

After mounting the fluid flow circuit to the centrifuge assembly, but before blood separation, the centrifuge chamber is primed to evacuate air from the chamber (and other conduits of the fluid flow circuit). This is done by conveying a priming fluid through the conduits and chamber of the fluid flow circuit, with the priming fluid forcing any air in the chamber and conduits to a more suitable location of the fluid flow circuit, such as a waste container.

Anticoagulant or saline (or a combination thereof) is most commonly used as a priming fluid (which approach may be referred to as a "solution prime"). It is also possible for the blood itself to serve as the priming fluid (which may be referred to as a "blood prime"), though this is less common due to concerns with possibly damaging the blood while in contact with air in the fluid flow circuit. Conventional priming approaches typically involve creation of pressure/vacuum, changing the direction of rotation of the centrifuge, and varying flow rates to evacuate the air, all of which increase the risk of damage to red blood cells.

Another reason why blood priming may be less favored than solution priming is that a volume of fluid much greater than the centrifuge chamber volume is typically required to ensure that all air has been evacuated. Hence, there is the concern that a blood prime may be "wasteful," as it increases the extracorporeal volume from a source during the first blood draw cycle. A blood prime also extends the time that a donor or patient is connected to the system compared to a solution prime, as a solution prime will typically be completed before the blood source is connected to the system.

There may, however, be disadvantages to solution priming. For example, a non-blood priming fluid must be returned to the blood source; otherwise, an additional waste container may need to be incorporated into the fluid flow circuit to receive the priming fluid. Further, solution priming requires the use of additional non-biological fluid, possibly rendering it more expensive than blood priming.

In view of the foregoing, an ideal priming approach may be a blood prime that requires less blood than is typically required to evacuate air from the centrifuge chamber. Such an approach would convey blood into the centrifuge chamber, evacuate air via plug flow (while avoiding damage to the blood), and then start blood separation without significant volume or steps to ensure that the centrifuge chamber is fully primed.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device includes a controller, a centrifuge configured to receive and rotate a continuous-flow centrifuge chamber of a fluid flow circuit, a pump system, an optical detection assembly, and a pressure sensor. The pump system is configured to convey fluid through the fluid flow circuit, while the optical detection assembly is configured to monitor low- and high-g outlet conduits connected to the centrifuge chamber and to transmit signals to the controller that are indicative of the nature of flow through the low- and high-g outlet conduits. The pressure sensor is configured to measure an inlet pressure of fluid flowing into the centrifuge chamber and to transmit signals to the controller that are indicative of the inlet pressure. The controller is configured to execute a priming procedure, which includes controlling the centrifuge to rotate the centrifuge chamber at an initial rotational rate and controlling the pump system to convey a priming fluid into the centrifuge chamber so as to convey air out of the centrifuge chamber via the low-g outlet conduit. The controller determines whether the priming fluid is flowing through the low-g outlet conduit and, upon determining that the priming fluid is flowing through the low-g outlet conduit, controls the centrifuge to increase the rate at which the centrifuge chamber is rotated so as to move air remaining in the centrifuge chamber toward the low-g outlet conduit. Next, the controller determines whether, at the increased rotational rate, the inlet pressure is less than a threshold value, a flow rate of the priming fluid through the low-g outlet conduit is decreasing, and a flow rate of the priming fluid through the high-g outlet conduit is increasing. Upon determining that, at the increased rotational rate, the inlet pressure is less than the threshold value, the flow rate of the priming fluid through the low-g outlet conduit is not decreasing, and the flow rate of the priming fluid through the high-g outlet conduit is not increasing, the controller ends the priming procedure.

In another aspect, a method is provided for priming a continuous-flow centrifuge chamber. The method includes rotating the centrifuge chamber at an initial rotational rate and conveying a priming fluid into the centrifuge chamber so as to convey air out of the centrifuge chamber via a low-g outlet conduit connected to the centrifuge chamber. It is then determined whether the priming fluid is flowing through the low-g outlet conduit and, upon determining that the priming fluid is flowing through the low-g outlet conduit, the rate at which the centrifuge chamber is rotated is increased so as to move air remaining in the centrifuge chamber toward the low-g outlet conduit. Next, it is determined whether, at the increased rotational rate, an inlet pressure of the priming fluid flowing into the centrifuge chamber is less than a threshold value, a flow rate of the priming fluid through the low-g outlet conduit is decreasing, and a flow rate of the priming fluid through a high-g outlet conduit connected to the centrifuge chamber is increasing. Upon determining that, at the increased rotational rate, the inlet pressure is less than the threshold value, the flow rate of the priming fluid through the low-g outlet conduit is not decreasing, and the flow rate of the priming fluid through the high-g outlet conduit is not increasing, the priming procedure is ended.

BRIEF DESCRIPTION OF THE DRAWINGS

FIG. 7 is a perspective view of the centrifugal separator of FIG. 3, with selected portions thereof broken away to show the light source and light detector of the interface monitoring assembly;

FIG. 14 is a perspective view of a prismatic reflector used in combination with the centrifuge chamber of FIGS. 8-10;

FIG. 15 is a perspective view of the pris alio reflector of FIG. 14, showing light being transmitted therethrough;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-21 show components of a blood or fluid processing system that embodies various aspects of the present subject matter. While the system may be described herein in terms of its use in separating blood into two or more components, it should be understood that systems according to the present disclosure can be used for processing a variety of biological or bodily fluids (including fluids containing both bodily and non-bodily fluids, such as anticoagulated blood), as well as non-bodily fluids.

Figure 1:
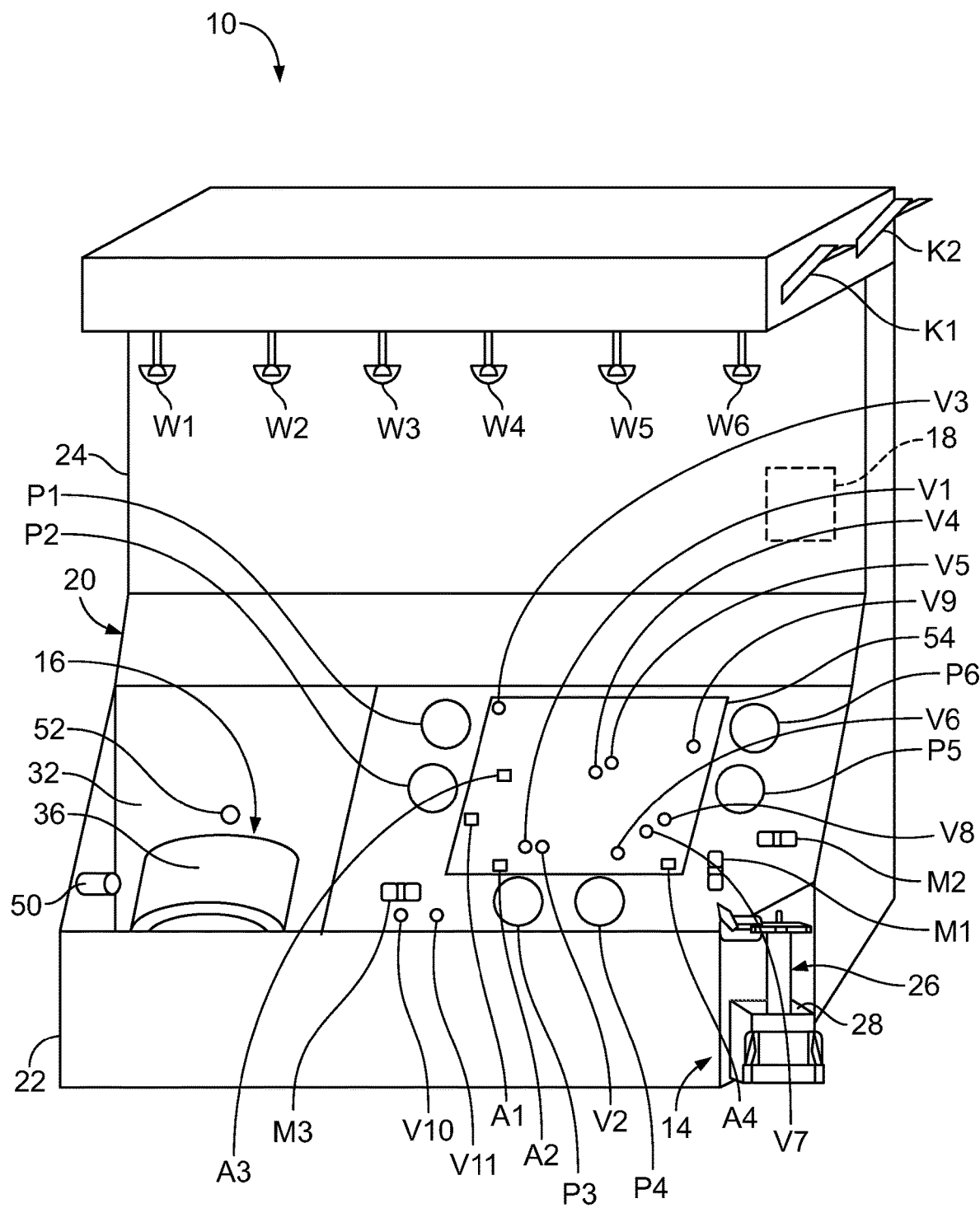
FIG. 1 is a perspective view of an exemplary fluid processing device that comprises a component of a fluid processing system according to an aspect of the present disclosure.
Figure 2:
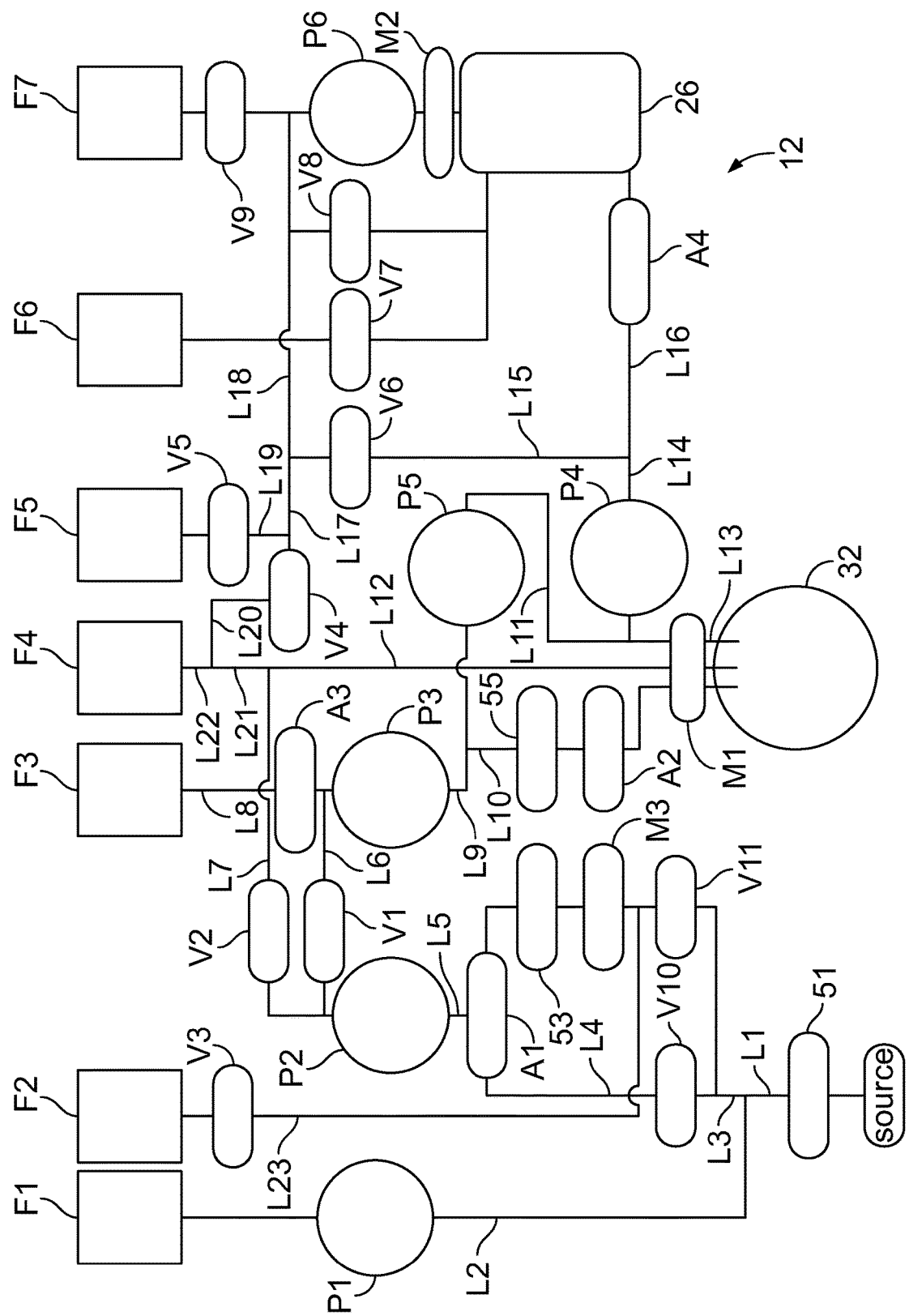
FIG. 2 is a schematic view of an exemplary disposable fluid flow circuit that may be mounted to the fluid processing device of FIG. 1 to complete a fluid processing system according to an aspect of the present disclosure.

Fluid processing systems according to the present disclosure typically include two principal components, a durable and reusable fluid processing device 10 (FIG. 1) and a disposable fluid flow circuit 12 (FIG. 2). The illustrated fluid processing device 10 includes a spinning membrane separator drive unit 14 (FIG. 1), a centrifuge or centrifugal separator 16 (FIG. 3), additional components that control fluid flow through the disposable flow circuit 12, and a controller 18 (FIG. 1), which governs the operation of the other components of the fluid processing device 10 to perform a procedure selected by the operator. The principles described herein regarding priming of a continuous-flow centrifuge chamber are not limited to any particular fluid processing systems or procedures, so no complete fluid processing devices or procedures will be described in detail herein. However, reference may be made to POT Patent Application Publication No. WO 2018/053217 A1 (which is hereby incorporated herein by reference) for a detailed description of the fluid processing device 10 of FIG. 1, along with various exemplary procedures that may be carried out using such a system.

I. The Durable Fluid Processing Device

The fluid processing device 10 (FIG. 1) is configured as a durable item that is capable of long-term use. It should be understood that the fluid processing device 10 of FIG. 1 is merely exemplary of one possible configuration and that fluid processing devices according to the present disclosure may be differently configured. For example, it is within the scope of the present disclosure for the fluid processing device to omit a spinning membrane separator drive unit 14.

In the illustrated embodiment, the fluid processing device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24.

A. Spinning Membrane Separator Drive Unit

The illustrated fluid processing device 10 includes a spinner support or spinning membrane separator drive unit 14 (FIG. 1) for accommodating a generally cylindrical spinning membrane separator 26 of a fluid flow circuit 12 (FIG. 2). U.S. Pat. No. 5,194,145 (which is hereby incorporated herein by reference) describes an exemplary spinning membrane separator drive unit that would be suitable for incorporation into the fluid processing device 10, but it should be understood that the spinning membrane separator drive unit 14 may be differently configured without departing from the scope of the present disclosure. The principles described herein are specific to priming of a continuous-flow centrifuge chamber received by the centrifugal separator 16, so the spinning membrane separator drive unit 14 is not described in detail herein.

B. Centrifugal Separator

Continuous-flow centrifuge chamber priming principles are described herein in the context of a detection assembly of the centrifugal separator 16, such that a particularly configured centrifugal separator 16 and associated continuous-flow centrifuge chamber or centrifugal separation chamber 32 will be described herein for illustrative purposes. However, it should be understood that such principles may be practiced in combination with differently configured centrifugal separators and/or continuous-flow centrifuge chambers, and that the principles described herein are not specific to the illustrated centrifuge chamber 32 and/or centrifugal separator 16.

Figure 3:
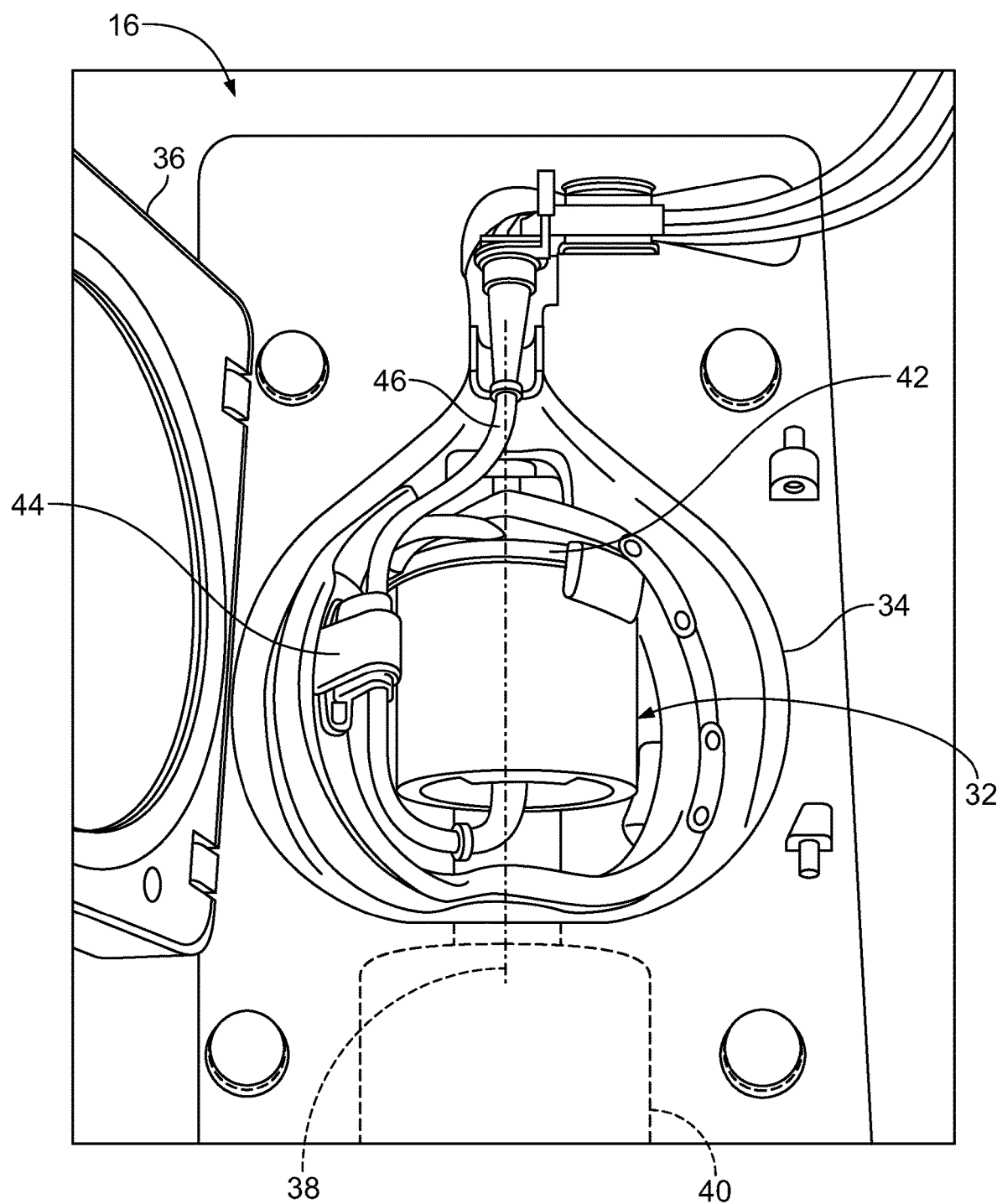
FIG. 3 is a perspective view of an exemplary centrifugal separator of the fluid processing device of FIG. 1, with the centrifuge chamber of a fluid flow circuit mounted therein.

The illustrated centrifugal separator 16 includes a centrifuge compartment 34 that may receive the other components of the centrifugal separator 16 (FIG. 3). The centrifuge compartment 34 may include a lid 36 that is opened to insert and remove a centrifuge chamber 32 of the fluid flow circuit 12. During a separation procedure, the lid 36 may be closed with the centrifuge chamber 32 positioned within the centrifuge compartment 34, as the centrifuge chamber 32 is spun or rotated about an axis 38 under the power of an electric drive motor or rotor 40 of the centrifugal separator 16.

Figure 4:
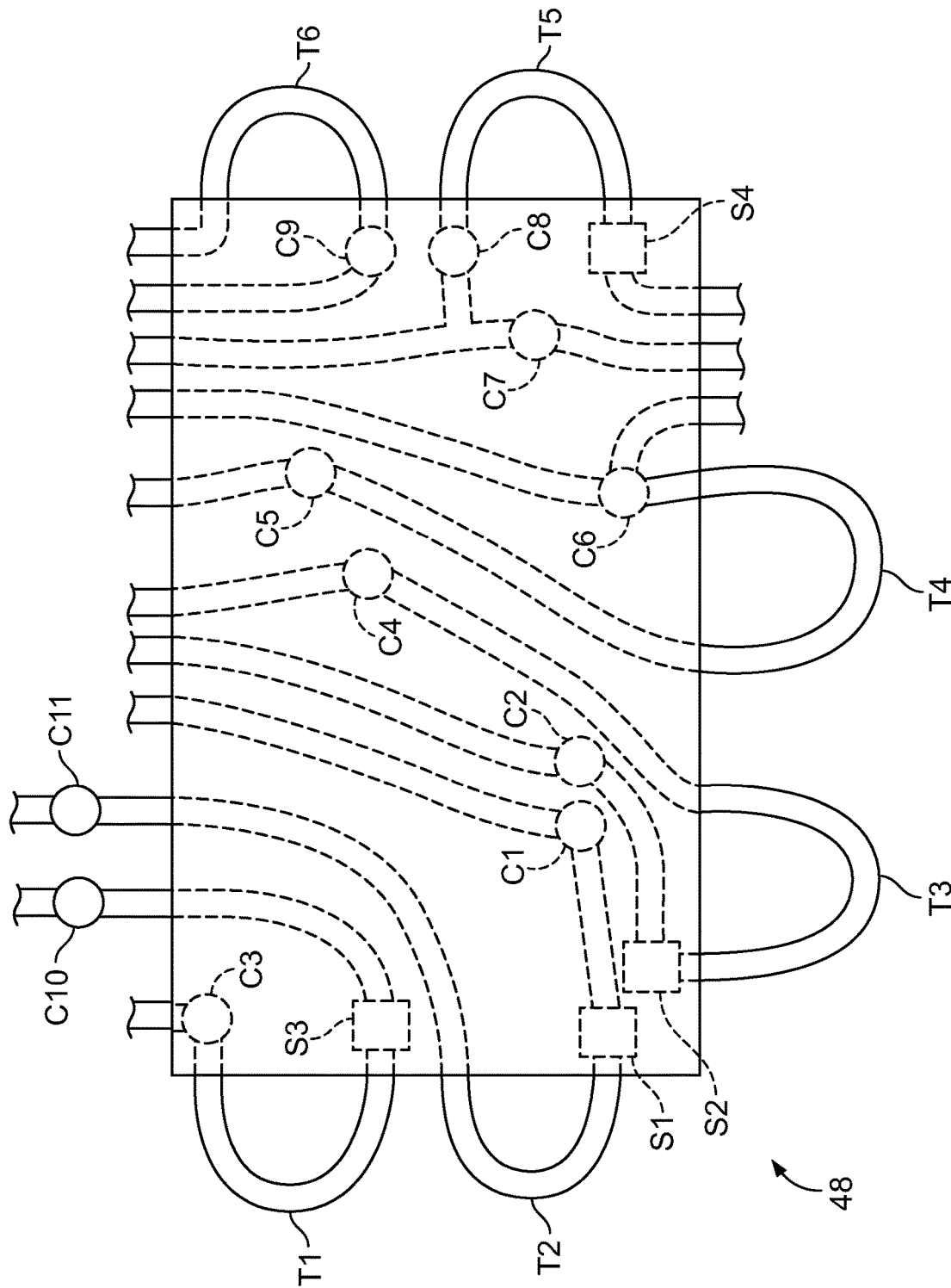
FIG. 4 is a top plan view of an exemplary cassette of a fluid flow circuit, which can be actuated to perform a variety of different fluid processing procedures in association with the fluid processing device shown in FIG. 1.

The particular configuration and operation of the centrifugal separator 16 depends upon the particular configuration of the centrifuge chamber 32 of the fluid flow circuit 12. In one embodiment, the centrifugal separator 16 is similar in structure and operation to that of the ALYX system manufactured by Fenwal, Inc. of Lake Zurich, Ill., which is an affiliate of Fresenius Kabi AG of Bad Homburg, Germany, as described in greater detail in U.S. Pat. No. 8,075,468, which is hereby incorporated herein by reference. More particularly, the centrifugal separator 16 may include a carriage or support 42 that holds the centrifuge chamber 32 and a yoke member 44. The yoke member 44 engages an umbilicus 46 of the fluid flow circuit 12, which extends between the centrifuge chamber 32 and a cassette 48 of the fluid flow circuit 12 (FIG. 4). The yoke member 44 causes the umbilicus 46 to orbit around the centrifuge chamber 32 at a one omega rotational speed. The umbilicus 46 twists about its own axis as it orbits around the centrifuge chamber 32. The twisting of the umbilicus 46 about its axis as it rotates at one omega with the yoke member 44 imparts a two omega rotation to the centrifuge chamber 32, according to known design. The relative rotation of the yoke member 44 at a one omega rotational speed and the centrifuge chamber 32 at a two omega rotational speed keeps the umbilicus 46 untwisted, avoiding the need for rotating seals.

Figure 6:
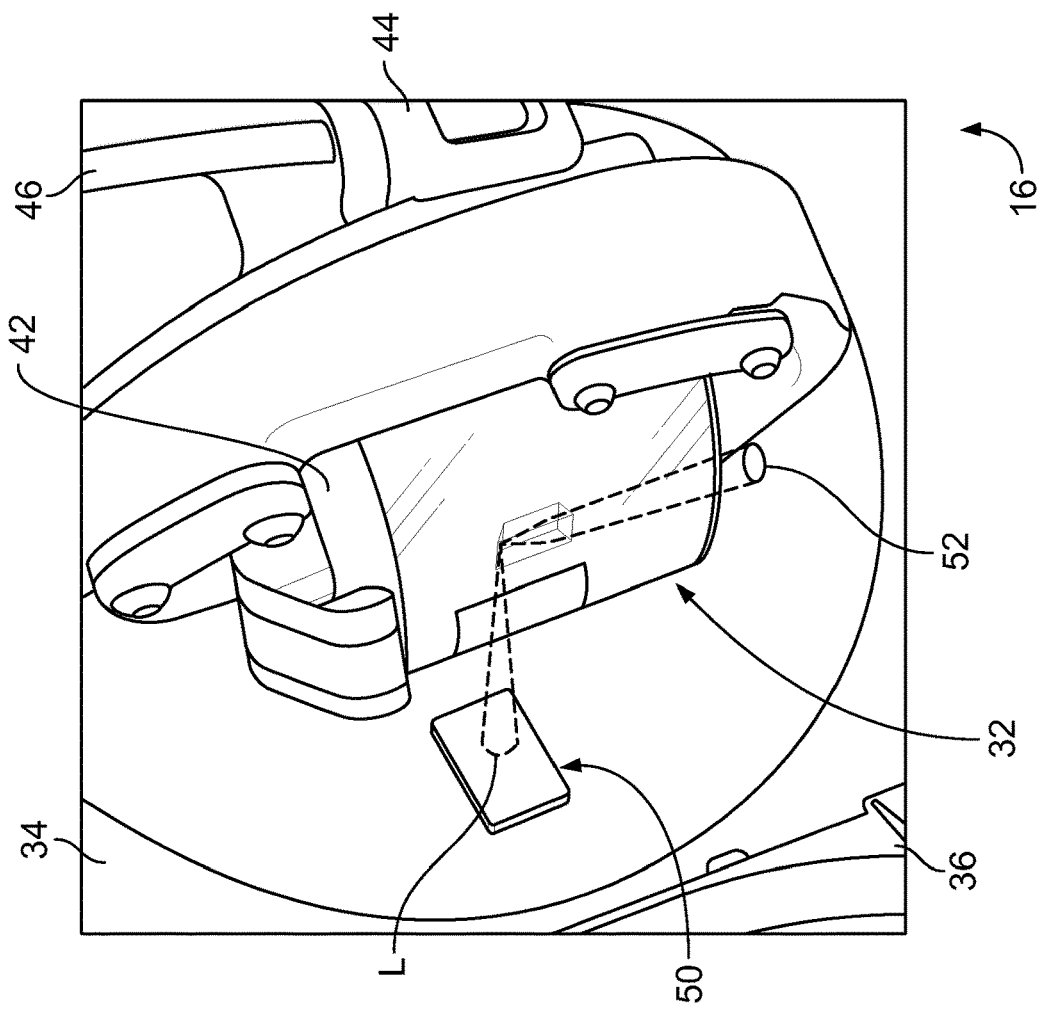
FIG. 6 is a perspective view of the centrifugal separator of FIG. 3, with the light source operating to transmit a light beam to a light detector of the interface monitoring assembly.
Figure 5:
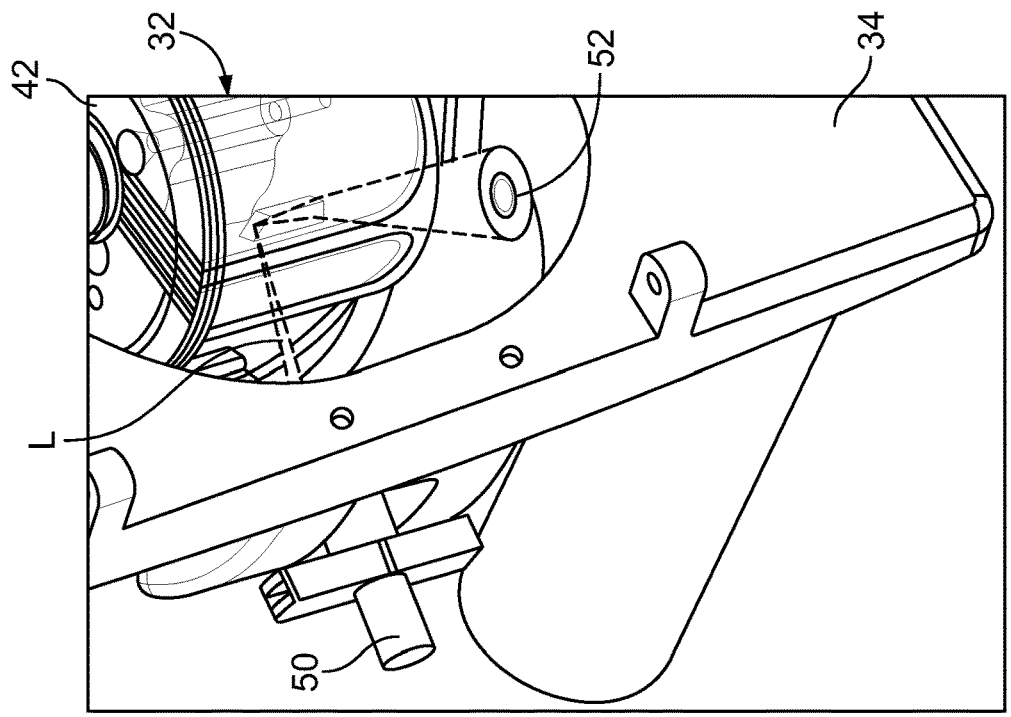
FIG. 5 is a perspective view of the centrifugal separator of FIG. 3, with selected portions thereof broken away to show a light source of an interface monitoring assembly.

A fluid is introduced into the centrifuge chamber 32 by the umbilicus 46, with the fluid being separated (e.g., into a layer of less dense components, such as platelet-rich plasma, if the fluid is blood, and a layer of more dense components, such as packed red blood cells, if the fluid is blood) within the centrifuge chamber 32 as a result of centrifugal forces as it rotates. Components of an interface monitoring assembly may be positioned within the centrifuge compartment 16 to oversee separation of fluid within the centrifuge chamber 32. As shown in FIGS. 5-7, the interface monitoring assembly may include a light source 50 and a light detector 52, which is positioned and oriented to receive at least a portion of the light emitted by the light source 50. The illustrated light source 50 and light detector 52 are associated with stationary surfaces of the centrifuge compartment 34, but either or both may instead be associated with a movable structure or component of the fluid processing device 10, as in U.S. Pat. No. 5,316,667, which is hereby incorporated herein by reference.

The orientation of the various components of the interface monitoring system depends at least in part on the particular configuration of the centrifuge chamber 32, which will be described in greater detail herein. In general, though, the light source 50 emits a light beam "L" (e.g., a laser light beam) through the separated fluid components within the centrifuge chamber 32 (which may be formed of a material that substantially transmits the light L or at least a particular wavelength of the light L without absorbing it). A portion of the light L reaches the light detector 52, which transmits a signal to the controller 18 that is indicative of the location of an interface between the separated fluid components. If the controller 18 determines that the interface is in the wrong location (which can affect the separation efficiency of the centrifugal separator 16 and/or the quality of the separated blood components), then it can issue commands to the appropriate components of the fluid processing device 10 to modify their operation so as to move the interface to the proper location.

C. Other Components of the Fluid Processing Device

In addition to the spinning membrane separator drive unit 14 and the centrifugal separator 16, the fluid processing device 10 may include other components compactly arranged to aid fluid processing.

The generally horizontal portion 22 of the case 20 of the illustrated fluid processing device 10 includes a cassette station 54, which accommodates a cassette 48 of the fluid flow circuit 12 (FIG. 4). In one embodiment, the cassette station 54 is similarly configured to the cassette station of U.S. Pat. No. 5,868,696 (which is incorporated herein by reference), but is adapted to include additional components and functionality. The illustrated cassette station 54 includes a plurality of clamps or valves V1-V9 (FIG. 1), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 2 and 4). Depending on the configuration of the fluid flow circuit 12, its cassette 48 may not include a valve station C1-C9 for each valve V1-V9 of the cassette station 54, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-09, thereby allowing fluid flow through that port or ports). Additional clamps or valves V10 and V11 may be positioned outside of the cassette station 54 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 54 and cassette 48 may be differently configured and operate differently from the valves V10 and V11 and valve stations C10 and C11 that are spaced away from the cassette station 54.

The cassette station 54 may be provided with additional components, such as pressure sensors A1-A4, which interact with sensor stations S1-S4 of the cassette 48 to monitor the pressure at various locations of the fluid flow circuit 12. For example, if the fluid source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifuge chamber 32. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The fluid processing device 10 may also include a plurality of pumps P1-P6 (which may be collectively referred to as a pump system) to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 4) and may be selectively operated under command of the controller 18 to cause fluid to flow through a portion of the fluid flow circuit 12, as will be described in greater detail. In one embodiment, all or a portion of the cassette station 54 may be capable of translational motion in and out of the case 20 to allow for automatic loading of the tubing loops T1-T6 into the associated pump P1-P6.

The illustrated fluid processing device 10 also includes an optical detection assembly or centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the nature of flow into and out of the centrifuge separator 16 (e.g., whether air or a liquid flow is flowing through an inlet or outlet conduit connected to the centrifuge chamber 32, whether fluid is flowing through such conduit or is stagnant, etc.) and use the signals to optimize the separation procedure. If one or more properties of a fluid flowing into or out of the centrifuge chamber 32 is outside of an acceptable range, then the controller 18 may initiate an alarm or error condition to alert an operator to the condition. Exemplary optical detection assemblies are described in U.S. Pat. No. 6,419,822 and U.S. Patent Application Publication No. 2019/0369008 (both of which are hereby incorporated herein by reference), but it should be understood that a different approach may also be employed for optically monitoring fluid flow into and out of the centrifugal separator 16.

The illustrated fluid processing device 10 further includes a spinner outlet sensor M2, which accommodates tubing of the fluid flow circuit 12 that flows a separated substance out of the spinning membrane separator 26. The spinner outlet sensor M2 monitors the substance to determine one or more properties of the substance, and may do so by optically monitoring the substance as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated fluid processing device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F7 of the fluid flow circuit 12 (FIG. 2). The containers F1-F7 receive fluid components or waste products separated during processing or assorted non-biological fluids (e.g., priming fluids, intravenous fluids, or additive fluids). Each weight scale W1-W6 transmits to the controller 18 a signal that is indicative of the weight of the fluid within the associated container F1-F7 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports K1 and K2 that may support various components of the fluid flow circuit 12 or other suitably sized and configured objects.

D. Controller

As described above, the fluid processing device 10 includes a controller 18, which is suitably configured and/or programmed to control operation of the fluid processing device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid processing device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications (e.g., plasma exchange, red blood cell exchange, and photopheresis) can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid processing device 10, conveying fluid through the fluid flow circuit 12 to a location for separation (i.e., into the spinning membrane separator 26 or the centrifuge chamber 32 of the fluid flow circuit 12), separating the fluid into two or more components as desired, and conveying the separated components into storage containers, to a second location for further separation (e.g., into whichever of the spinning membrane separator 26 and centrifuge chamber 32 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump to convey fluid through a portion of the fluid flow circuit 12 at a particular flow rate. Hence, while it may be described herein that a particular component of the fluid processing device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid processing device 10 to monitor various aspects of the operation of the fluid processing device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the light detector 52 of the interface monitoring assembly and the centrifugal separator sensor M1. The signals that the controller 18 receives from the light detector 52 are indicative of the location of an interface between the separated fluid components within the centrifuge chamber 32, while the signals from the centrifugal separator sensor M1 indicate whether the target interface location should be adjusted. If the controller 18 determines that the interface is in the wrong location, then it can issue commands to the appropriate components of the fluid processing device 10 to modify their operation so as to move the interface to the proper location. For example, the controller 18 may instruct the pump system to cause fluid to flow into the centrifuge chamber 32 at a different rate and/or for a separated fluid component to be removed from the centrifuge chamber 32 at a different rate and/or for the centrifuge chamber 32 to be spun at a different speed by the centrifugal separator 16.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 2), it is intended to be a sterile, single use, disposable item. Before beginning a given procedure, the operator loads various components of the fluid flow circuit 12 in the case 20 in association with the fluid processing device 10. The controller 18 implements the procedure based upon preset protocols, taking into account other input from the operator. Upon completing the procedure, the operator removes the fluid flow circuit 12 from association with the fluid processing device 10. The portions of the fluid flow circuit 12 holding the collected fluid component or components (e.g., collection containers or bags) are removed from the case 20 and retained for storage, immediate use, or further processing. The remainder of the fluid flow circuit 12 is removed from the case 20 and discarded.

A variety of different disposable fluid flow circuits may be used in combination with the fluid processing device 10, with the appropriate fluid flow circuit depending on the procedure to be carried out using the system. Generally speaking, though, the fluid flow circuit 12 includes a cassette 48 (FIG. 4) to which the other components of the fluid flow circuit 12 are connected by flexible tubing or conduits. The other components may include a plurality of fluid containers F1-F7 (for holding fluid to be processed, a separated fluid component, a priming fluid, or an additive solution, for example), one or more fluid source access devices (e.g., a connector for accessing fluid within a fluid container), a centrifuge chamber 32 (FIGS. 8-10), and (optionally) a spinning membrane separator 26.

B. Cassette and Tubing

The cassette 48 (FIG. 4) provides a centralized, programmable, integrated platform for all the pumping and many of the valving functions required for a given fluid processing procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 54 of the fluid processing device 10, with a flexible diaphragm of the cassette 48 placed into contact with the cassette station 54. The flexible diaphragm overlays an array of interior cavities formed by the body of the cassette 48. The different interior cavities define sensor stations S1-S4, valve stations C1-C9, and a plurality of flow paths or conduits. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 54, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the fluid processing device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, as will be described in greater detail. Certain procedures require fewer than all of the sensor stations, valve stations, and/or tubing loops illustrated in the exemplary cassette 48 of FIG. 4, such that it should be understood that the cassettes of different fluid flow circuits 12 may be differently configured (e.g., with fewer sensor stations, valve stations, and/or tubing loops) without departing from the scope of the present disclosure.

Additional tubing or conduits extend from the side surface of the cassette 48 to connect to the other components of the fluid flow circuit 12, such as the various fluid containers F1-F7, the spinning membrane separator 26, and the centrifuge chamber 32. The number and content of the various fluid containers F1-F7 depends upon the procedure for which the fluid flow circuit 12 is used, so they will be described in greater detail with respect to an exemplary procedure. The tubing connected to the centrifuge chamber 32 (which includes one inlet conduit and two outlet conduits) may be aggregated into an umbilicus 46 (FIG. 3) that is engaged by the yoke member 44 of the centrifugal separator 16 (as described above) to cause the umbilicus 46 to orbit around and spin or rotate the centrifuge chamber 32 during a separation procedure.

Various additional components may be incorporated into the tubing leading out of the cassette 48 or into one of the cavities of the cassette 48. For example, as shown in FIG. 2, a manual clamp 51 may be associated with a line or lines leading to the fluid source and/or fluid recipient, a return line filter 53 (e.g., a microaggregate filter) may be associated with a line leading to a fluid recipient, filters may be positioned upstream of one or more of the fluid containers to remove a substance (e.g., leukocytes) from a separated component (e.g., red blood cells) flowing into the fluid container, and/or an air trap 55 may be positioned on a line upstream of the centrifuge chamber 32.

C. Centrifuge Chamber

Figure 8:
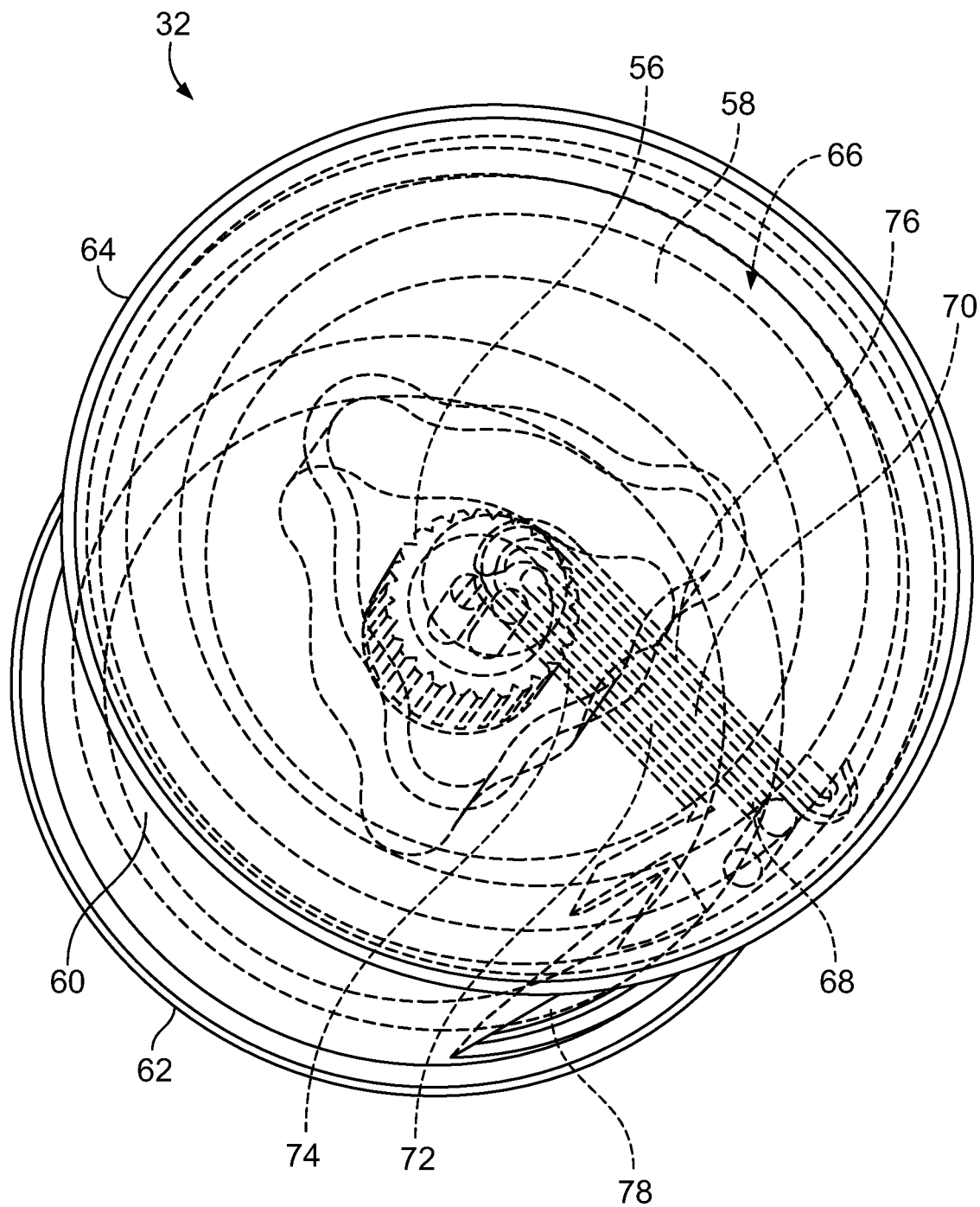
FIG. 8 is a perspective view of an exemplary centrifuge chamber of a fluid flow circuit.
Figure 9:
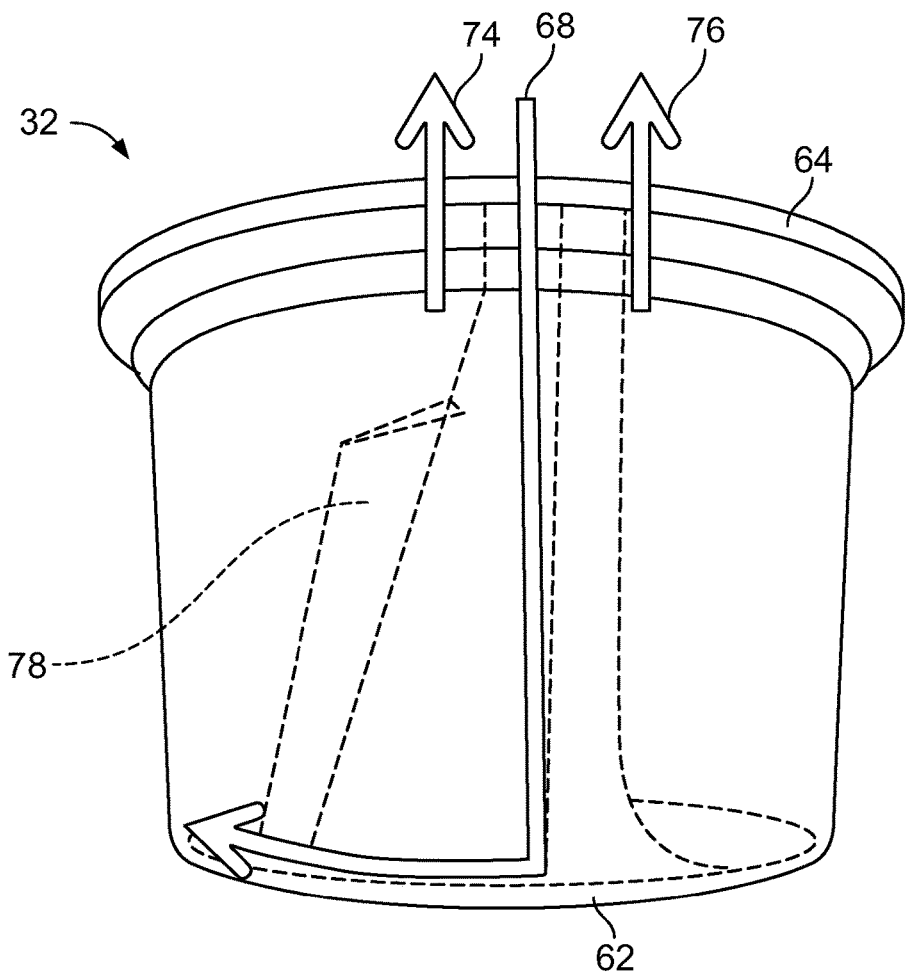
FIG. 9 is a front elevational view of the centrifuge chamber of FIG. 8.
Figure 10:
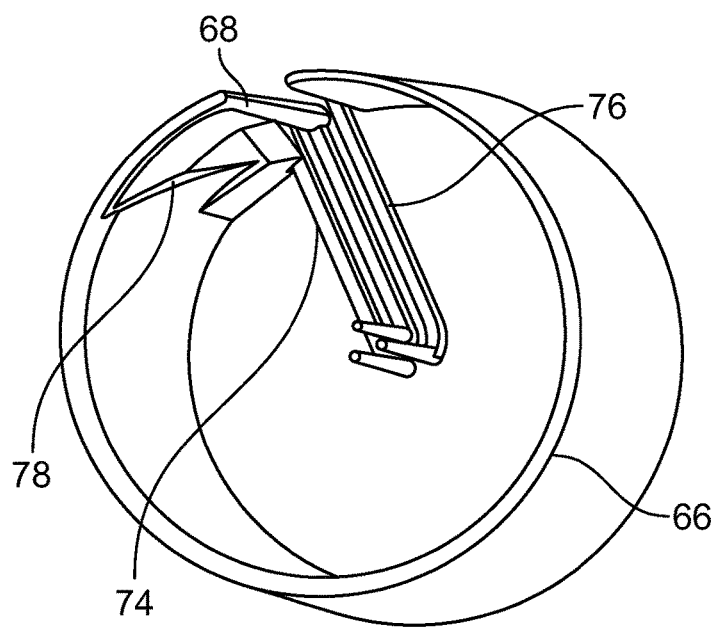
FIG. 10 is a bottom perspective view of the fluid flow path through the centrifuge chamber of FIG. 8.

An exemplary centrifuge chamber 32 is shown in FIGS. 8 and 9, while FIG. 10 illustrates the fluid flow path defined by the centrifuge chamber 32. In the illustrated embodiment, the body of the centrifuge chamber 32 is pre-formed in a desired shape and configuration (e.g., by injection molding) from a rigid, biocompatible plastic material, such as a non-plasticized medical grade acrylonitrile-butadiene-styrene (ABS). All contours, ports, channels, and walls that affect the fluid separation process are preformed in a single, injection molded operation. Alternatively, the centrifuge chamber 32 can be formed by separate molded parts, either by nesting cup-shaped subassemblies or two symmetric halves.

The underside of the centrifuge chamber 32 includes a shaped receptacle 56 that is suitable for receiving an end of the umbilicus 46 of the fluid flow circuit 12 (FIG. 3). A suitable receptacle 56 and the manner in which the umbilicus 46 may cooperate with the receptacle 56 to deliver fluid to and remove fluid from the centrifuge chamber 32 are described in greater detail in U.S. Pat. No. 8,075,468.

The illustrated centrifuge chamber 32 has radially spaced apart inner (low-g) and outer (high-g) side wall portions 58 and 60, a bottom or first end wall portion 62, and a cover or second end wall portion 64. The cover 64 comprises a simple flat part that can be easily welded or otherwise secured to the body of the centrifuge chamber 32. Because all features that affect the separation process are incorporated into one injection molded component, any tolerance differences between the cover 64 and the body of the centrifuge chamber 32 will not affect the separation efficiencies of the centrifuge chamber 32. The wall portions 58 and 60, the bottom 62, and the cover 64 together define an enclosed, generally annular channel 66 (FIG. 10).

An inlet 68 communicating with the channel 66 is defined between opposing interior radial walls 70 and 72. One of the interior walls 70 joins the outer (high-g) wall portion 60 and separates the upstream and downstream ends of the channel 66. The interior walls 70 and 72 define the inlet passageway 68 of the centrifuge chamber 32 which, in one flow configuration, allows fluid to flow from the umbilicus 46 to the upstream end of the channel 66.

The illustrated centrifuge chamber 32 further includes first and second outlets 74 and 76, respectively, which may be defined by opposing surfaces of interior radial walls. Both the first and second outlets 74 and 76 extend radially inward from the channel 66. The first (low-g) outlet 74 extends radially inward from an opening which, in the illustrated embodiment, is located at the inner side wall portion 58, while the second (high-g) outlet 76 extends radially inward from an opening that is associated with the outer side wall portion 60. The illustrated first outlet 74 is positioned adjacent to the inlet 68 (near the upstream end of the channel 66), while the second outlet 76 may be positioned at the opposite, downstream end of the channel 66.

It should be understood that the centrifuge chamber 32 illustrated in FIG. 8 is merely exemplary and that the centrifuge chamber 32 may be differently configured without departing from the scope of the present disclosure. For example, POT Patent Application Publication No. WO 2018/053217 A1 describes other exemplary centrifuge chamber configurations that may be used in combination with the priming principles described herein.

III. Centrifugal Separation and Interface Detection Principles

Fluid flowed into the channel 66 separates into an optically dense layer "R" and a less optically dense layer "P" (FIGS. 11-13) as the centrifuge chamber 32 is rotated about the rotational axis 38. The optically dense layer R forms as larger and/or heavier fluid particles move under the influence of centrifugal force toward the outer (high-g) wall portion 60. If the fluid being separated is blood, the optically dense layer R will typically include red blood cells but, depending on the speed at which the centrifuge chamber 32 is rotated, other cellular components (e.g., larger white blood cells) may also be present in the optically dense layer R.

If the fluid being separated is blood, the less optically dense layer P typically includes a plasma constituent, such as platelet-rich plasma or platelet-poor plasma. Depending on the speed at which the centrifuge chamber 32 is rotated and the length of time that the blood is resident therein, other components (e.g., smaller white blood cells and anticoagulant) may also be present in the less optically dense layer P.

In one embodiment, fluid introduced into the channel 66 via the inlet 68 will travel in a generally clockwise direction (in the orientation of FIG. 8) as the optically dense layer R separates from the less optically dense layer P. The optically dense layer R continues moving in the clockwise direction as it travels the length of the channel 66 along the outer side wall portion 60, from the upstream end to the downstream end, where it exits the channel 66 via the second outlet 76. The less optically dense layer P separated from the optically dense layer R reverses direction, moving counterclockwise along the inner side wall portion 58 to the first outlet 74, adjacent to the inlet 68.

Figure 11:
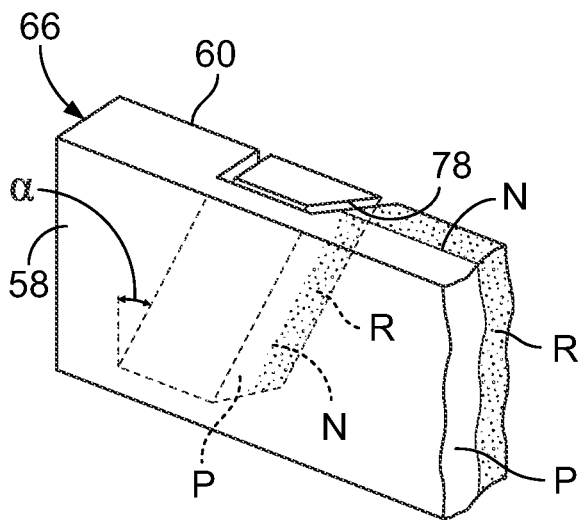
FIG. 11 is an enlarged perspective view of a portion of a channel of the centrifuge chamber of FIGS. 8-10, with an interface between separated fluid components being positioned at a (typically) desired location on a ramp defined within the channel.
Figure 12:
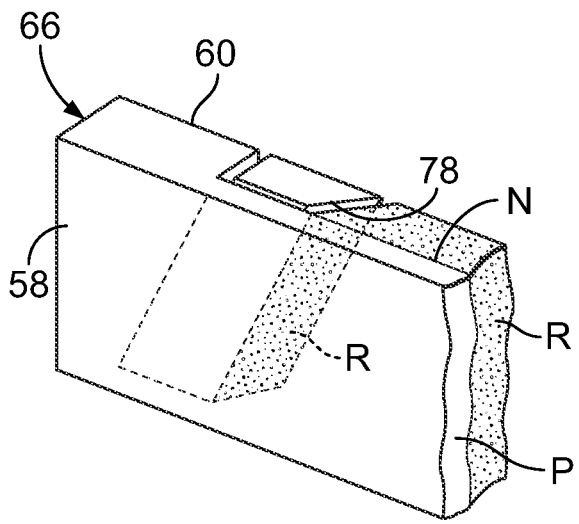
FIG. 12 is an enlarged perspective view of the channel and ramp of FIG. 11, with the interface being at a (typically) undesired high location on the ramp.
Figure 13:
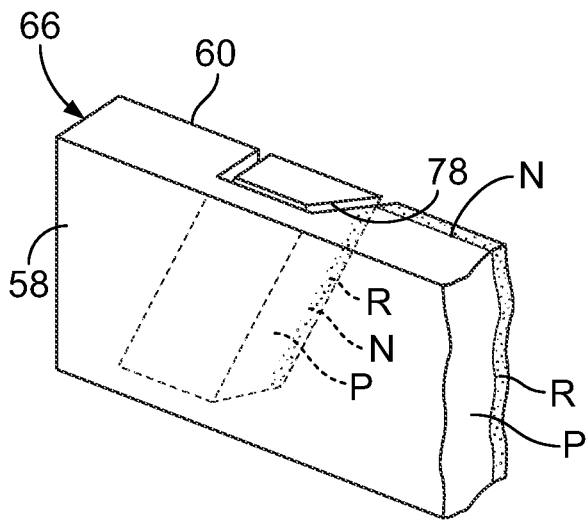
FIG. 13 is an enlarged perspective view of the channel and ramp of FIG. 11, with the interface being at a (typically) undesired low location on the ramp.

The transition between the optically dense layer R and the less optically dense layer P may be referred to as the interface "N". If the fluid being separated is blood, a buffy coat containing mononuclear cells and peripheral blood stem cells may be located at the interface N. The location of the interface N within the channel 66 of the centrifuge chamber 32 can dynamically shift during fluid processing, as FIGS. 11-13 show. If the location of the interface N is too high (that is, if it is too close to the inner side wall portion 58 and the first outlet 74, as in FIG. 12), red blood cells can flow into the first outlet 74, potentially adversely affecting the quality of the low density components (platelet-rich plasma or platelet-poor plasma). On the other hand, if the location of the interface N is too low (that is, if it resides too far away from the inner wall portion 58, as FIG. 13 shows), the collection efficiency of the system may be impaired. The ideal or target interface location may be experimentally determined, which may vary depending on any of a number of factors (e.g., the configuration of the centrifuge chamber 32, the rate at which the centrifuge chamber 32 is rotated about the rotational axis 38, etc.).

As described above, the fluid processing device 10 may include interface monitoring assembly (including the light source 50 and the light detector 52), a centrifugal separator sensor M1, and a controller 18 with an interface control module to monitor and, as necessary, adjust or correct the position of the interface N. In the illustrated embodiment, the centrifuge chamber 32 is formed with a ramp 78 extending from the high-g wall portion 60 at an angle α across at least a portion of the channel 66 (FIGS. 8 and 11-13). The angle α, measured with respect to the rotational axis 38 is about 25° in one embodiment. FIGS. 11-13 show the orientation of the ramp 78 when viewed from the low-g side wall portion 58 of the centrifuge chamber 32. Although it describes a flexible separation chamber, the general structure and function of the ramp 78 may be better understood with reference to U.S. Pat. No. 5,632,893, which is hereby incorporated herein by reference. The ramp 78 may be positioned at any of a number of locations between the upstream and downstream ends of the channel 66, but in one embodiment, the ramp 78 may be positioned generally adjacent to the first outlet 74, in the path of fluid and/or a fluid component moving from the inlet 68 to the first outlet 74.

The ramp 78 makes the interface N between the optically dense layer R and the less optically dense layer P more discernible for detection, displaying the optically dense layer R, less optically dense layer P, and interface N for viewing through a light-transmissive portion of the centrifuge chamber 32. To that end, the ramp 78 and at least the portion of the centrifuge chamber 32 angularly aligned with the ramp 78 may be formed of a light-transmissive material, although it may be advantageous for the entire centrifuge chamber 32 to be formed of the same light-transmissive material.

In the illustrated embodiment, the light source 50 of the interface monitoring system is associated with a fixture or wall of the centrifuge compartment 34 and oriented to emit a light L that is directed toward the rotational axis 38 of the centrifugal separator 16, as shown in FIGS. 5-7. If the light detector 52 is positioned at an angle with respect to the light source 50 (as in the illustrated embodiment), the light L emitted by the light source 50 must be redirected from its initial path before it will reach the light detector 52. In the illustrated embodiment, the light L is redirected by a reflector that is associated with a light-transmissive portion of the inner side wall portion 58, as shown in FIGS. 5 and 6. The reflector may be a separate piece that is secured to the inner side wall portion 58 (e.g., by being bonded thereto) or may be integrally formed with the body of the centrifuge chamber 66.

In one embodiment, the reflector may be a reflective surface, such as a mirror, that is oriented (e.g., at a 45° angle) to direct light L emitted by the light source 50 to the light detector 52. In another embodiment, the reflector is provided as a prismatic reflector 80 (FIGS. 7, 14, and 15), which is formed of a light-transmissive material (e.g., a clear plastic material) and has inner and outer walls 82 and 84 and first and second end walls 86 and 88 (FIG. 14). The inner wall 82 is positioned against the inner side wall portion 58 of the centrifuge chamber 32 and is oriented substantially perpendicular to the initial path of the light L from the light source 50. This allows light L from the light source 50 to enter into the prismatic reflector 80 via the inner wall 82 while continuing along its initial path. The light L continues through the prismatic reflector 80 along its initial path until it encounters the first end wall 86, The first end wall 86 is oriented at an angle (e.g., an approximately 45° angle) with respect to the inner wall 82 and the second end wall 88, causing the light L to be redirected within the prismatic reflector 80, rather than exiting the prismatic reflector 80 via the first end wall 86.

The first end wall 86 directs the light L at an angle to its initial path (which may be an approximately 90° angle, directing it from a path toward the rotational axis 38 to a path that is generally parallel to the rotational axis 38) toward the second end wall 88 (FIG. 15), The first end wall 86 and the inner and outer walls 82 and 84 of the prismatic reflector 80 may be configured to transmit the redirected light L from the first end wall 86 to the second end wall 88 by total internal reflection. The second end wall 88 is oriented substantially perpendicular to the redirected path of the light L through the prismatic reflector 80, such that the light L will exit the prismatic reflector 80 via the second end wall 88, continuing along its redirected path. In one embodiment, the second end wall 88 is roughened or textured or otherwise treated or conditioned to diffuse the light L as it exits the prismatic reflector 80, which may better ensure that the light L reaches the light detector 52 (FIG. 7).

The prismatic reflector 80 may be angularly aligned with the ramp 78, such that the light L from the light source 50 will only enter into the prismatic reflector 80 when the ramp 78 has been rotated into the path of the light L. At all other times (when the ramp 78 is not in the path of the light L), the light L will not reach the prismatic reflector 80 and, thus, will not reach the light detector 52.

Upon the ramp 78 first being rotated into the path of the light L from the light source 50, the light L will begin to reach the prismatic reflector 80, which directs the light L to the light detector 52. This causes the voltage output of the light detector 52 (i.e., the signal transmitted from the light detector 52 to the controller 18) to increase to a non-zero value or state. The ramp 78 and prismatic reflector 80 are eventually rotated out of alignment with the light source 50, at which time no light L will reach the prismatic reflector 80 and the voltage output of the light detector 52 will return to a low- or zero-state.

During the time that the ramp 78 and prismatic reflector 80 are rotated through the path of the light L from the light source 50, the light L continues through the channel 66 and the fluids in the channel 66. At least a portion of the light L (i.e., the portion not absorbed or reflected by the fluids) exits the channel 66 by striking and entering a light-transmissive portion of the inner side wall portion 58. The light L passes through the inner side wall portion 58 and enters the prismatic reflector 80, which redirects the light L from its initial path to the light detector 52, as described above.

The light detector 52 generates a signal that is transmitted to the interface control module of the controller 18, which can determine the location of the interface N on the ramp 78, In one embodiment, the location of the interface N is associated with a change in the amount of light L that is transmitted through the less optically dense layer P and the optically dense layer R. For example, the light source 50 may be configured to emit a light L that is more readily transmitted by platelet-rich plasma or platelet-poor plasma than by red blood cells, such as red visible light (from a laser or a differently configured light source L), which is substantially absorbed by red blood cells. The less optically dense layer P and the optically dense layer R each occupy a certain portion of the ramp 78, with the light detector 52 receiving different amounts of light L depending on whether the light L travels through the less optically dense layer P on the ramp 78 or the optically dense layer R on the ramp 78, The percentage of the ramp 78 occupied by each layer is related to the location of the interface N in the channel 66. Thus, by measuring the amount of time that the voltage output or signal from the light detector 52 is relatively high (corresponding to the time during which the light L is passing through only the less optically dense layer P on the ramp 78), the controller 18 may determine the location of the interface N and take steps to correct the location of the interface N, if necessary, An exemplary approach to adjustment of the position of the interface N is described in greater detail in PCT Patent Application Publication No. WO 2018/053217 A1.

IV. Priming of Centrifuge Chamber

Depending on the fluid separation objectives, there is a suitable procedure for separating and collecting any of a variety of different fluid components, either alone or in combination with other fluid components. Accordingly, prior to processing, an operator selects the desired protocol (e.g., using an operator interface station, if provided), which informs the controller 18 of the manner in which it is to control the other components of the fluid processing device 10 during the procedure.

The operator may also proceed to enter various parameters. In the case of blood separation, this may include information regarding the blood source, along with the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the fluid processing device 10 (including the fluid containers F1-F7 being hung from the weight scales W1-W6 and the hooks or supports H1 and H2, as appropriate). An integrity check of the fluid flow circuit 12 may be executed by the controller 18 to ensure the various components are properly connected and functioning.

Following a successful integrity check, the fluid flow circuit 12 is primed to move air contained in the various conduits and in the centrifuge chamber 32 into a more suitable location (e.g., a waste container). If a fluid to be separated is used as a priming fluid (e.g., when the fluid flow circuit 12 is primed using blood prior to separation of the blood), the fluid source is fluidly connected to the fluid flow circuit 12. On the other hand, if some other priming fluid is employed (e.g., saline or anticoagulant, in the case of a blood separation procedure), the fluid source may be connected after the fluid flow circuit 12 has been primed. Thus, it should be understood that the priming principles described herein are not limited to use with any particular priming fluid.

A. Fluid Flow Circuit

FIG. 2 is a schematic view of an exemplary fluid flow circuit 12 having a single fluid access device (e.g., a phlebotomy needle) for alternately drawing fluid into the fluid flow circuit 12 and conveying fluid out of the fluid flow circuit 12. It should be understood that the illustrated fluid flow circuit 12 is merely exemplary and that the priming principles described herein may be employed with differently configured fluid flow circuits. This may include fluid flow circuits having a pair of fluid access devices, with one dedicated to drawing fluid into the fluid flow circuit and other being dedicated to conveying fluid out of the fluid flow circuit.

The illustrated fluid flow circuit 12 includes a cassette 48 of the type described above and illustrated in FIG. 4, which connects the various components of the fluid flow circuit 12. The various connections amongst the components of the fluid flow circuit 12 are shown in FIG. 2, which also shows the fluid flow circuit 12 mounted to the fluid processing device 10.

The fluid flow circuit 12 of FIG. 2 includes seven fluid containers F1-F7. Most of the fluid containers are not used when priming the centrifuge chamber 32, but only during a fluid separation procedure that follows priming of the centrifuge chamber 32. Hence, the nature and of number of the fluid containers may vary without departing from the scope of the present disclosure. In the illustrated embodiment, the fluid flow circuit 12 is configured for separation of blood into red blood cells, platelet-poor plasma, and platelet concentrate. In this case, one of the fluid containers F1 contains an anticoagulant fluid and, thus, may be referred to as an anticoagulant bag. In the illustrated priming procedure, in which blood is used to prime the centrifuge chamber 32, anticoagulant from the anticoagulant bag F1 is added to blood drawn into the fluid flow circuit 12 from a blood source. In other embodiments, in which some other fluid is used to prime the centrifuge chamber 32, blood is not drawn into the fluid flow circuit 12 during the priming stage and, thus, the anticoagulant bag F1 is not used during the priming stage (unless the centrifuge chamber 32 is to be primed using anticoagulant from the anticoagulant bag F1, which is within the scope of the present disclosure). A second fluid container F2 contains saline or the like and, thus, may be referred to as a saline bag. The saline bag F2 is not used in the illustrated priming procedure but, in other embodiments in which blood is not used to prime the centrifuge chamber 32, saline from the saline bag F2 may be used during the priming stage to prime the centrifuge chamber 32 (as will be described herein).

The other illustrated containers include an in-process bag F3, a return bag F4, a platelet-poor plasma bag F5, a platelet concentrate bag F6, and a platelet additive solution bag F7. During a blood draw stage of a blood separation procedure, the in-process bag F3 receives a portion of the blood drawn into the fluid flow circuit 12, with the remainder of the blood being directed into the centrifuge chamber 32. During a return stage of a blood separation procedure, the in-process bag F3 acts as a source for blood to be conveyed into the centrifuge chamber 32 (allowing for continued blood separation during the return stage), while fluid (e.g., separated red blood cells) is returned to the blood source. The platelet-poor plasma bag F5 and the platelet concentrate bag F6 receive separated blood components during a separation procedure, while a storage or additive solution (such as PAS) may be added to the platelets in the platelet concentrate bag F6 from the platelet additive solution bag F7. As will be described in greater detail, the in-process bag F3 and the return bag F4 may be used during a priming procedure, whereas the platelet-poor plasma bag F5, the platelet concentrate bag F6, and the platelet additive solution bag F7 are typically not used.

B. First Phase

Figure 16:
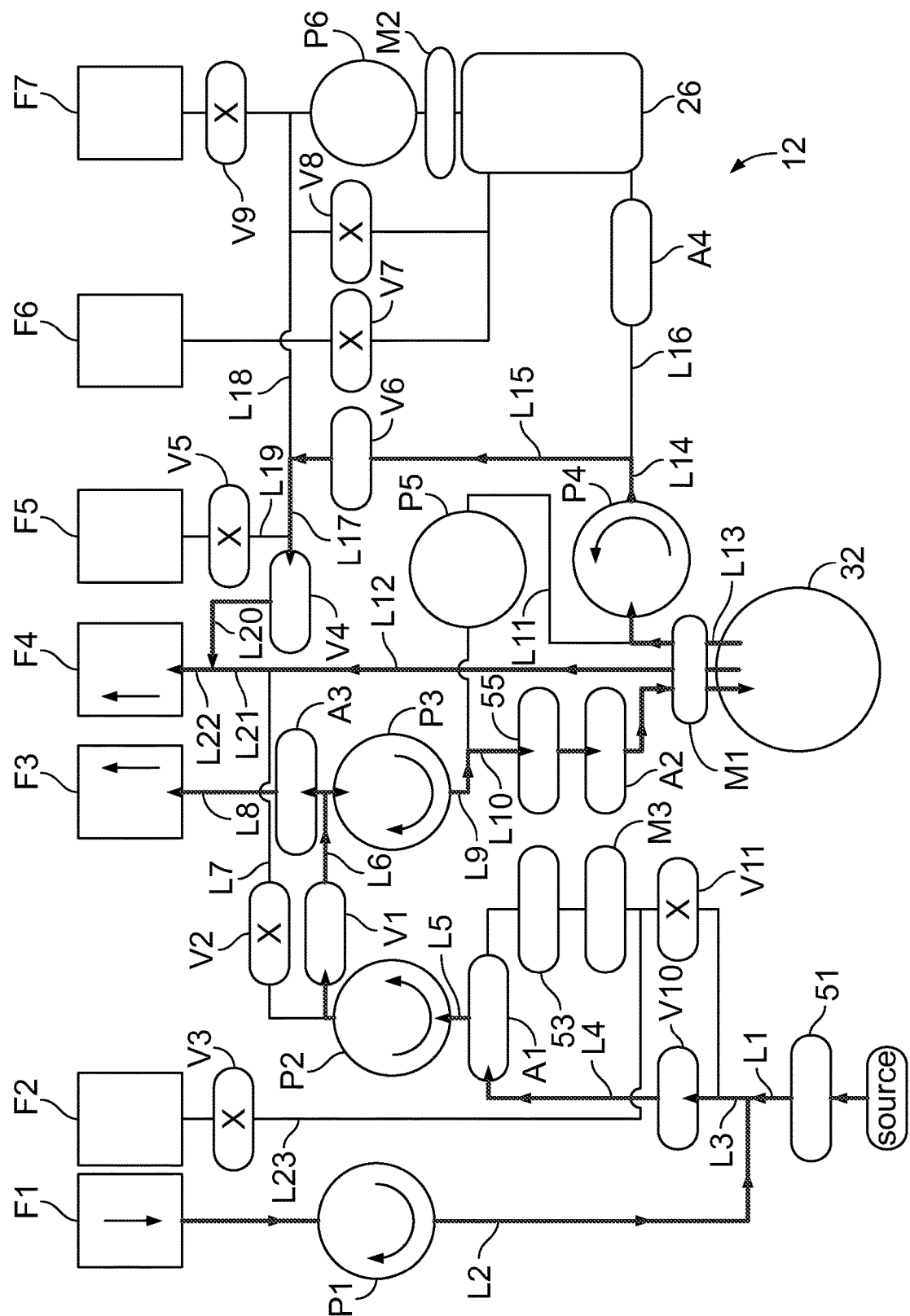
FIG. 16 is a schematic view of the fluid flow circuit of FIG. 2 mounted on the fluid processing device of FIG. 1, showing the system carrying out different fluid flow tasks in connection with priming a centrifuge chamber.
Figure 17:
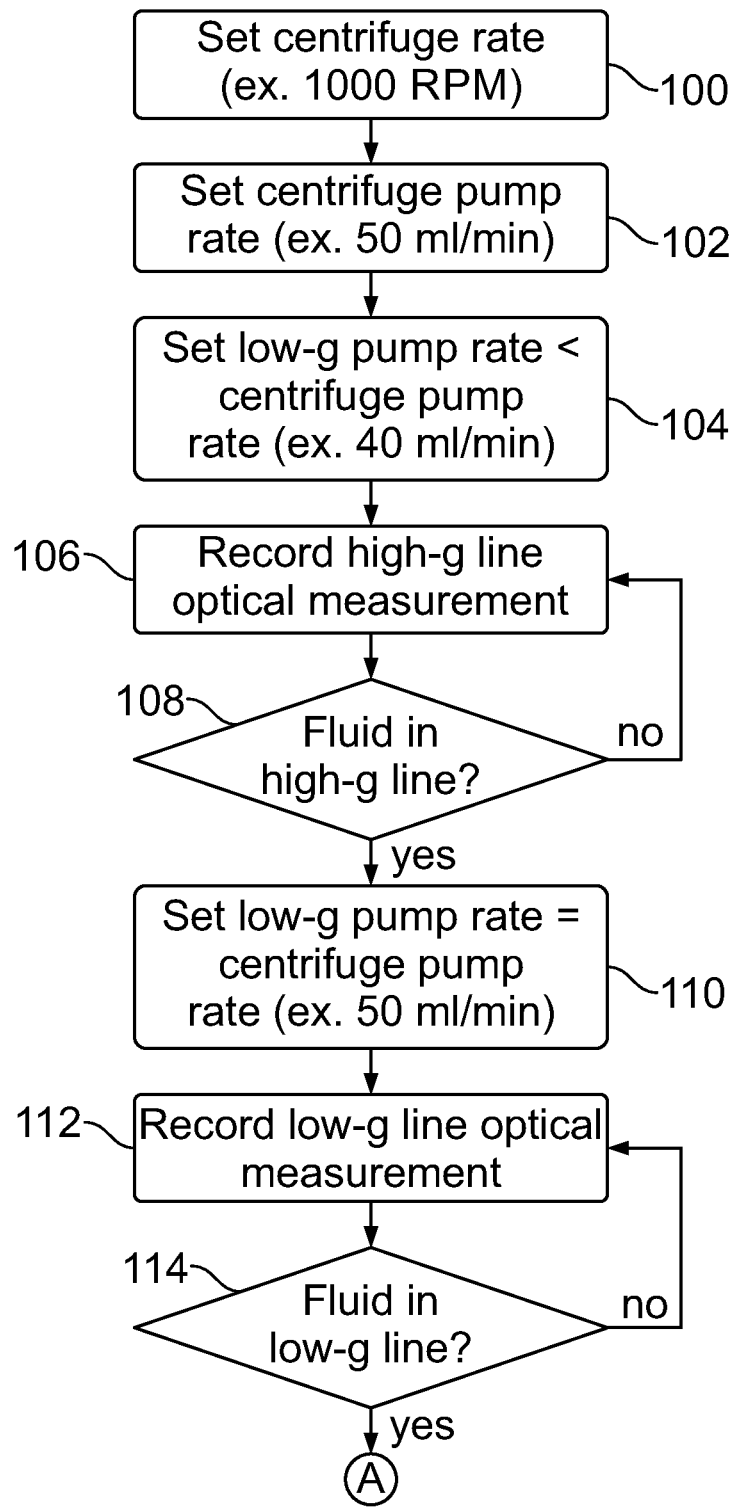
FIG. 17 is a flowchart of an exemplary approach to priming a centrifuge chamber according to an aspect of the present disclosure.
Figure 17:
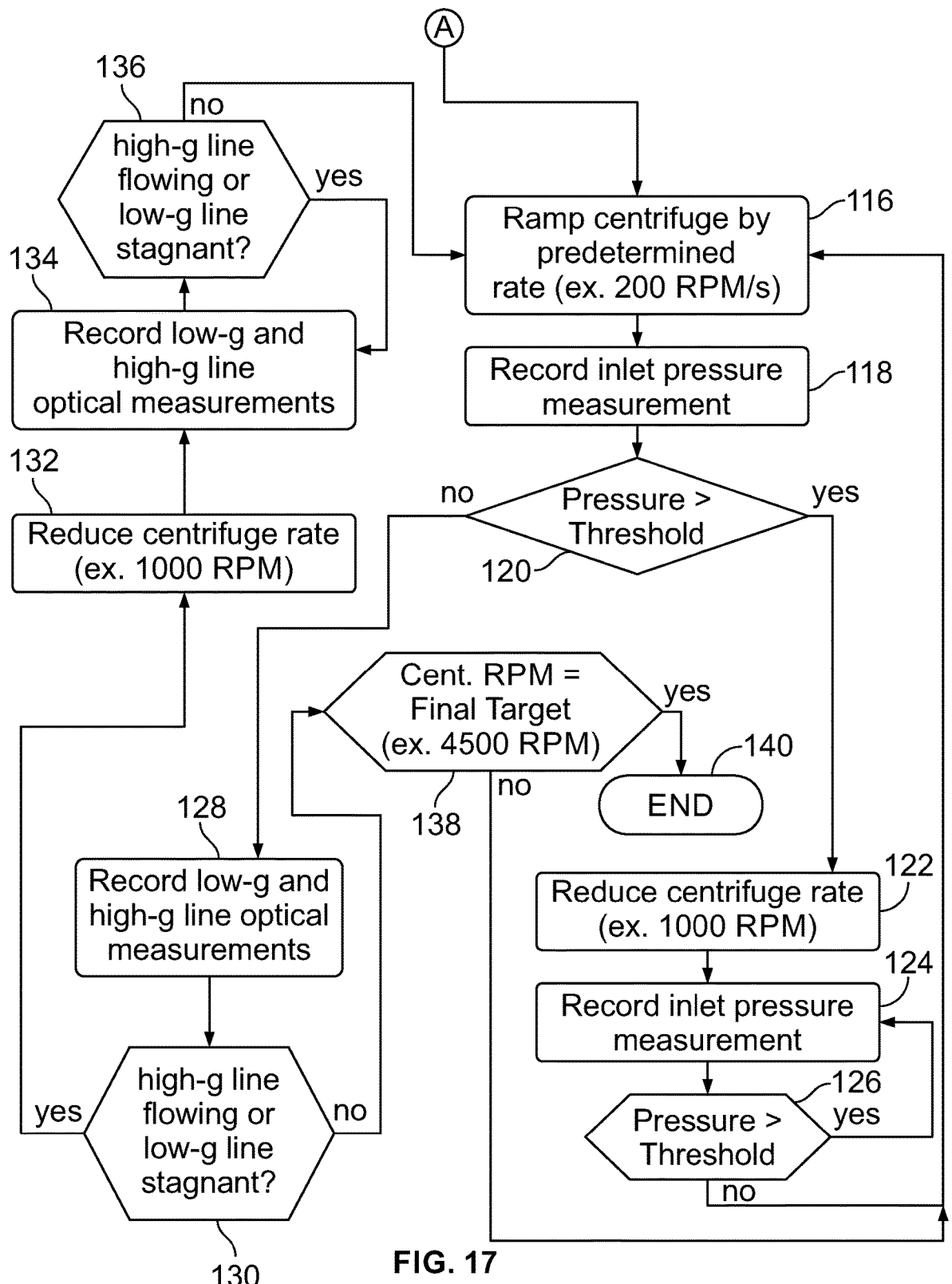

Fluid flow through the fluid flow circuit 12 during a first phase of an exemplary priming procedure is shown in FIG. 16, with steps 100-114 of FIG. 17 illustrating the various commands issued by the controller 18 to the other components of the fluid processing device 10 during the first phase and the various parameters and conditions that are analyzed by the controller 18 before advancing to the second phase of the priming procedure.

During the first phase, the controller 18 commands the centrifugal separator 16 to rotate the centrifuge chamber 32 received therein at an initial rotation rate (step 100 of FIG. 17). A relatively low rotation rate (e.g., on the order of approximately 1,000 rpm) may be advantageous in order to create enough g-force to ensure that the air in the centrifuge chamber 32 (which includes aft already present in the centrifuge chamber 32, along with aft moved into the centrifuge chamber 32 from other conduits of the fluid flow circuit 12 by fluid flowing toward the centrifuge chamber 32) is forced towards the low-g (radially inner) wall of the centrifuge chamber 32. Higher centrifuge rotation rates, such as 4,500 rpm (which may be required for blood separation) may be undesirable as air blocks (in which air gets stuck and cannot be forced out of the centrifuge chamber 32, causing pressure to rise) are more likely at higher g-forces.

In the illustrated embodiment, blood is drawn into the fluid flow circuit 12 from a blood source. If the blood source is a donor, then blood may be drawn into the fluid flow circuit 12 through a single needle that is connected to the cassette 48 by line L1. The line L1 may include a manual clamp 51 that may initially be in a closed position to prevent fluid flow through the line L1. When the priming procedure is to begin, an operator may move the manual clamp 51 from its closed position to an open position to allow fluid flow through the line L1. The term "line" is used herein to refer to any fluid flow conduit, whether a flexible tube that is connected to the cassette 48 or a rigidly defined flow path of the cassette 48, and a particular line is not limited to a flexible conduit or a rigidly defined conduit unless stated to the contrary.

The blood is drawn into the line L1 by a pump P2 of the fluid processing device 10, which may be referred to as the source pump. As described above, the source pump P2 may be a peristaltic pump that interacts with a tubing loop T2 extending from the cassette 48 of the fluid flow circuit 12. Anticoagulant may be added to the blood (such that the term "blood" as used herein should be understood to encompass blood with or without anticoagulant added thereto) via line L2 under action of a pump P1 of the fluid processing device 10 (which may be referred to as the anticoagulant pump). The anticoagulant pump P1 may be a peristaltic pump that interacts with a tubing loop T1 of the fluid flow circuit 12 to draw anticoagulant from the anticoagulant bag F1, through line L2, and to a junction of lines L1 and L2, where it is mixed with blood flowing into the fluid flow circuit 12.

In the illustrated embodiment, the valve V10 associated with valve station C10 is open, while the valve V11 associated with valve station C11 is closed, which directs the anticoagulated blood into and through lines L3 and L4 and a sensor station S1 associated with pressure sensor A1 of the fluid processing device 10. If the blood source is a living body (e.g., a donor), the pressure sensor A1 may communicate with the controller 18 to monitor the pressure within the vein of the blood source.

The blood flows from line L4 into line L5 and to a junction, where lines L6 and L7 meet line L5. The cassette 48 includes two valve stations C1 and C2 downstream of the source pump P2, which are associated with valves V1 and V2 (respectively) of the fluid processing device 10. One valve V2 is closed to prevent fluid flow through the associated valve station C2 (and line L7), while the other valve V1 is open to allow fluid flow through the associated valve station C1 The blood flows through the line L6 associated with the open valve V1 to another junction, where a portion of the blood is directed through line L8 into the in-process bag F3 and the remainder is directed through line L9 toward the centrifuge chamber 32. Line L9 is associated with a pump P3 (which may be referred to as a centrifuge pump), which controls the amount of blood that is directed to the centrifuge chamber 36 instead of the in-process bag F3. In particular, the flow rate of the source pump P2 is greater than the flow rate of the centrifuge pump P3, with the difference therebetween being equal to the flow rate of blood into the in-process bag F3. The flow rates may be selected such that the in-process bag F3 is partially or entirely filled with blood at the end of the priming procedure. In an exemplary embodiment, the controller 18 commands the centrifuge pump P3 to operate at a rate of approximately 50 ml/min (step 102 of FIG. 17).

The blood flowing through line L9 toward the centrifuge chamber 32 comes to a junction, where lines L10 and L11 meet line L9. The pump P5 (which may be referred to as a recirculation pump) associated with line L11 is inactive during the priming procedure, such that the blood flowing though line L9 is directed into line L10. The blood flowing through line L10 (which may be referred to as an inlet conduit) passes through an air trap 55, a sensor station S2 associated with pressure sensor A2 (which monitors the pressure of the blood flowing into the centrifuge chamber 32), and a centrifugal separator sensor M1 before entering the centrifuge chamber 32 via inlet 68.

Figure 18:
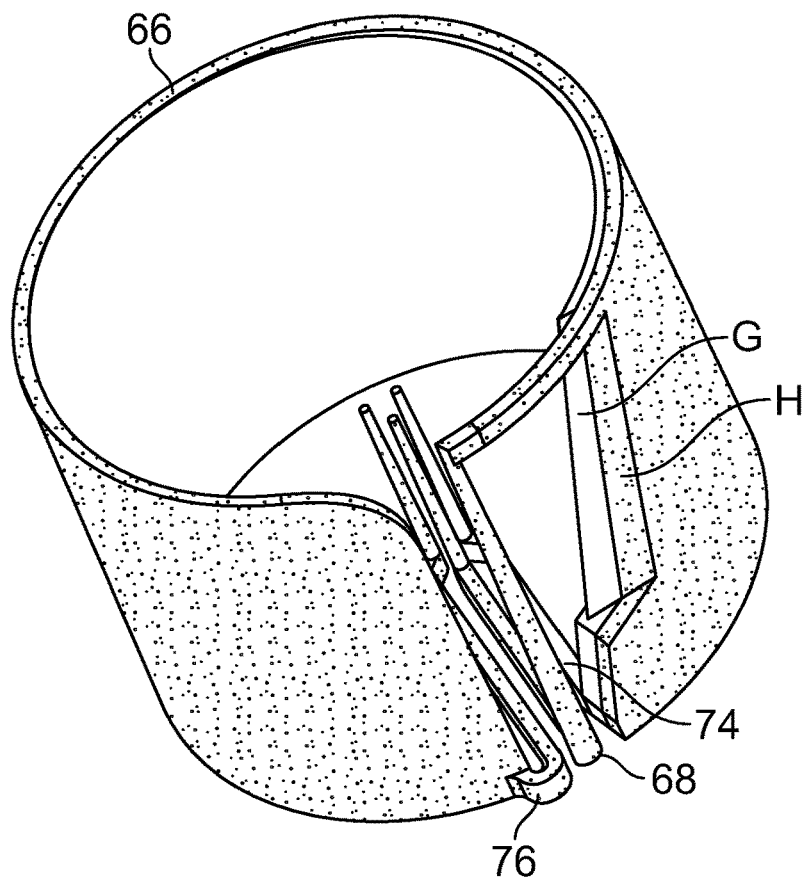
FIG. 18 is a bottom perspective view of the fluid flow path through the centrifuge chamber of FIGS. 8-10 during a priming procedure.
Figure 19:
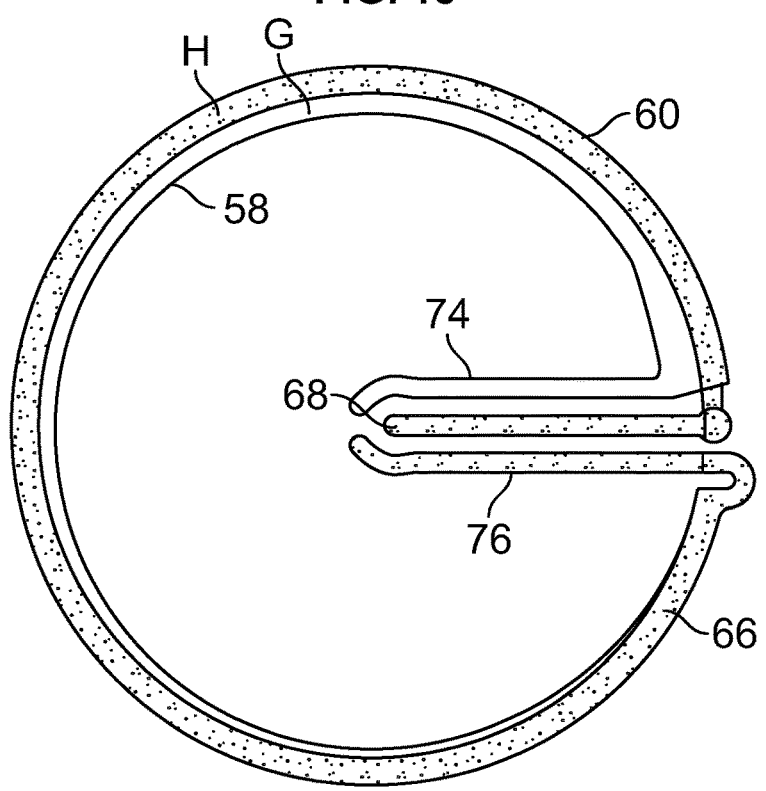
FIG. 19 is a bottom plan view of the fluid flow path through the centrifuge chamber of FIGS. 8-10 during a priming procedure.

The centrifuge chamber 32 is rotated slowly enough that the blood flowing through the channel 66 is not separated into its constituents, but rather is forced toward the high-g wall portion 60, while aft is allowed to flow freely from the centrifuge chamber 32. This flow arrangement is illustrated in FIGS. 18 and 19, which show blood "H" being forced toward the high-g wall portion 60 and air "G" being forced toward the low-g wall portion 58. The blood flowing along the high-g wall portion 60 exits the centrifuge chamber 32 via the high-g outlet 76 and associated line L12 (which may be referred to as a high-g outlet conduit), while the air exits the centrifuge chamber 32 via the low-g outlet 74 and associated line L13 (which may be referred to as a low-g outlet conduit).

As described above, the recirculation pump P5 is inactive during the priming procedure, which directs the air flowing through line L13 into line L14. While the recirculation pump P5 is inactive, the pump P4 (which may be referred to as a low-g pump) associated with line L14 is active during the priming procedure and controls the rate at which the air exits the centrifuge chamber 32, The low-g pump P4 conveys the air to a junction at which line L14 meets line L15 and line L16. The valve V7 associated with valve station C7 and the valve V8 associated with valve station C8 are closed, while the valve V6 associated with line L15 is open. A sixth pump P6 downstream of line L16 is inactive, thereby directing the air from line L14 into line L15.

The air flowing through line L15 arrives at a junction with lines L17 and L18. The valve V9 associated with valve station C9 is closed, which causes the air to flow from line L15 into line L17 and to another junction, where line L17 meets line L19 and line L20. The valve V5 associated with valve station C5 is closed, while the valve V4 associated with valve station C4 is open, which directs the air from line L17 into line L20 and to a junction with lines L21 and L22. Both lines L21 and L22 are open to fluid flow, but (as will be described) blood will be flowing through line L21 in the direction of line L22, which causes the air flowing through line L20 to enter line L22 and flow into the return bag F4 (along with the blood).

As can be seen in FIG. 16, there is no pump associated with line L12, but rather the blood exiting the centrifuge chamber 32 via the high-g outlet 76 will flow through line L12 at a rate equal to the difference between the operational rates of the centrifuge pump P3 and the low-g pump P4. The low-g pump P4 is initially operated at a rate that is slightly less than the rate of the centrifuge pump P3 in order to force blood out of the centrifuge chamber 32 via high-g outlet 76 and line L12. In an exemplary embodiment, the low-g pump P4 is operated at approximately 40 ml/min (per step 104 of FIG. 17), while the centrifuge pump P3 operates at approximately 50 ml/min (per step 102 of FIG. 17), thereby forcing blood out of the centrifuge chamber 32 at a rate of approximately 10 ml/min (i.e., the 40 ml/min operational rate of the low-g pump P4 subtracted from the 50 ml/min operational rate of the centrifuge pump P3).

The blood flowing through line L12 arrives at a junction where line L12 meets line L7 and line L21. As described above, the valve V2 associated with valve station C2 is closed, which directs the blood from line L12 into line L21 and then to a junction at which line L11 meets line L20 and line L22. As also described above, at this junction, the blood flowing through line L21 will join the air flowing through line L20 and together flow into the return bag F4.

As illustrated in FIG. 17 as step 106, the controller 18 analyzes signals from the centrifugal separator sensor M1 to assess the nature of flow through line L12 and determine when blood is present in line L12 (per step 108 of FIG. 17). This may be determined by the controller 18 according any suitable approach without departing from the scope of the present disclosure. In one embodiment, the centrifugal separator sensor M1 includes a light source that is configured to emit light through line L12, with the light being received by a light detector, which transmits a signal to the controller 18. Blood flowing through line L12 will allow less light to be transmitted through line L12 than the amount of light that is transmitted through an empty conduit, such that the magnitude of the signal from the light detector to the controller 18 will decrease upon blood flowing into and through line L12. Thus, upon receiving a lower magnitude signal from the light detector, the controller 18 may determine that blood is present in line L12.

Upon determining that blood is present in line L12 (and, hence, that line L12 has been primed), the controller 18 advances to step 110 of FIG. 17, in which the operational rate of the low-g pump P4 is increased from its first or initial rate to a higher second rate. In the illustrated embodiment, the controller 18 commands the low-g pump P4 to operate at the same rate as the centrifuge pump P3 (e.g., at approximately 50 ml/min in the embodiment of FIG. 17). Equating the operational rates of the centrifuge pump P3 and the low-g pump P4 causes all of the blood entering the centrifuge chamber 32 to exit the centrifuge chamber 32 via the low-g outlet 74 and line L13, effectively preventing blood from exiting the centrifuge chamber 32 via the high-g outlet 76 and line L12.

As illustrated in FIG. 17 as step 112, the controller 18 analyzes signals from the centrifugal separator sensor M1 to assess the nature of flow through line L13 and determine when blood is present in line L13 (per step 114 of FIG. 17). This may be determined by the controller 18 according any suitable approach without departing from the scope of the present disclosure. In one embodiment, the centrifugal separator sensor M1 includes a second light source that is configured to emit light through line L13, with the light being received by a second light detector, which transmits a signal to the controller 18. Blood flowing through line L13 will allow less light to be transmitted through line L13 than the amount of light that is transmitted through an empty conduit, such that the magnitude of the signal from the second light detector to the controller 18 will decrease upon blood flowing into and through line L13. Thus, upon receiving a lower magnitude signal from the second light detector, the controller 18 may determine that blood is present in line L13.

Blood flowing through line L13 means that line L13 has been primed and that (on account of plug flow) the centrifuge chamber 32 should be fully primed. However, it has been found that, as the centrifuge chamber 32 becomes filled with blood, it is typical for some air to become trapped in the centrifuge chamber 32. In order to ensure complete air evacuation from the centrifuge chamber 32, upon determining that blood is present in line L13 (the low-g outlet conduit) the controller 18 ends the first phase of the priming procedure and advances to a second phase.

C. Second Phase

The second phase of the priming procedure begins with step 116 of FIG. 17, in which the controller 18 commands the centrifugal separator 16 to rotate the centrifuge chamber 32 at a second rotational rate that is greater than the initial rotational rate (which initial rate is approximately 1,000 rpm in the illustrated embodiment), During the second phase, the centrifuge pump P3 and the low-g pump P4 continue to operate at the same rate, though they may be brought to a lower rate (e.g., on the order of 10-20 ml/min) to reduce the amount of blood that is required to complete air evacuation from the centrifuge chamber 32. If the operational rates of the centrifuge pump P3 and the low-g pump P4 are lowered, the operational rates of the other two active pumps P1 and P2 may also be lowered. The flow path established through the fluid flow circuit 12 in the first phase of the priming procedure (as shown in FIG. 16) remains the same during the second phase.

Figure 20:
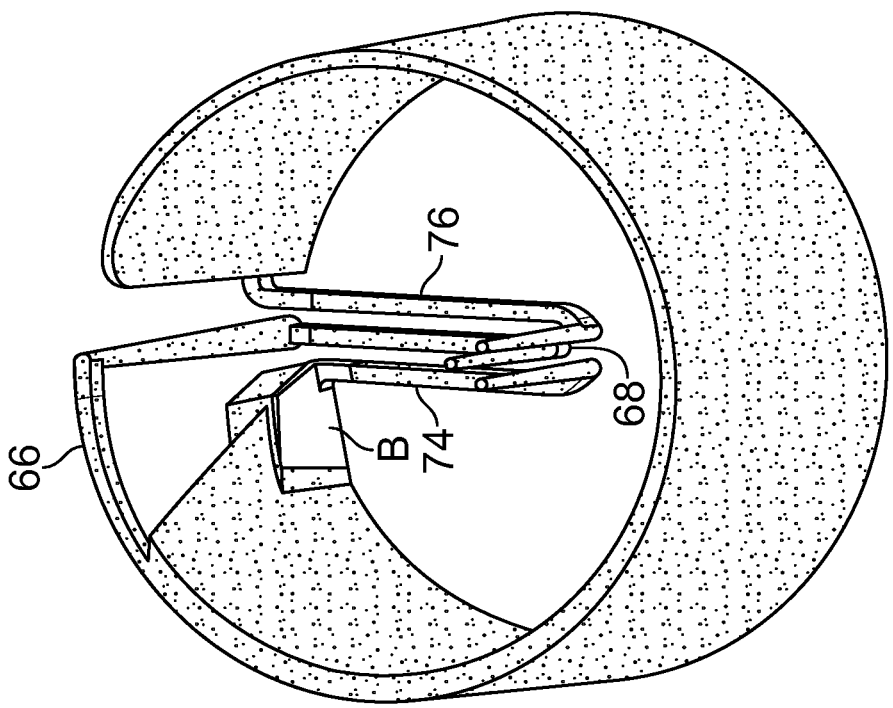
FIG. 20 is a bottom perspective view of the fluid flow path through the centrifuge chamber of FIGS. 8-10, with an air block adjacent to a low-g outlet port.

Increasing the rate at which the centrifuge chamber 32 is rotated will have the effect of moving any residual air remaining in the centrifuge chamber 32 (e.g., any air stuck to a chamber wall due to surface tension) toward the low-g outlet 74, as shown in FIG. 20 (with air being identified in FIG. 20 at "B"). The manner in which the rotational rate is increased may vary without departing from the scope of the present disclosure. In an exemplary embodiment, the rotational rate is increased at a predetermined rate, which is approximately 200 rpm/s in the embodiment shown in FIG. 17.

Figure 21:
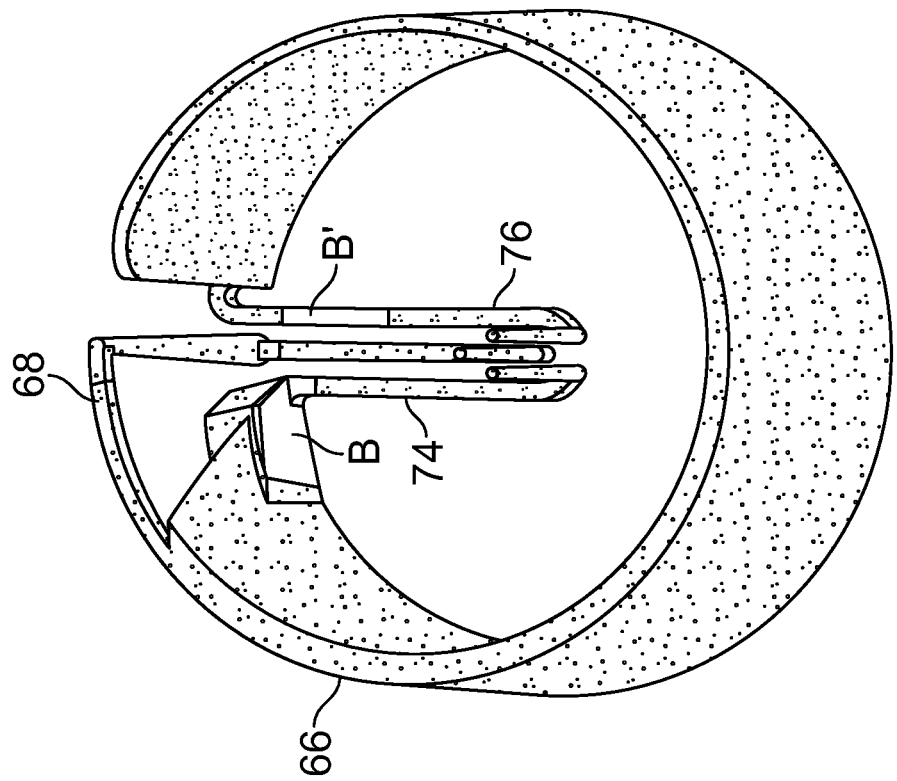
FIG. 21 is a bottom perspective view of the fluid flow path through the centrifuge chamber of FIGS. 8-10, with air blocks adjacent to low- and high-g outlet ports.

As shown in FIG. 17 as step 118, the controller 18 receives signals from the pressure sensor A2 while the centrifuge chamber 32 is rotated at an ever-increasing rate. The signals received by the controller 18 from the pressure sensor A2 are indicative of the pressure of the blood flowing into the centrifuge chamber 32. The controller 18 compares the inlet pressure to a threshold value (step 120 of FIG. 17) to ensure that the inlet pressure remains below the threshold value. The threshold value (which may be any value without departing from the scope of the present disclosure) is selected to be indicative of air blocks "B" and "B" being present at both the low-g outlet 74 and the high-g outlet 76, as shown in FIG. 21. Air blocks B and B' at both the low-g outlet 74 and the high-g outlet 76 prevent blood from exiting the centrifuge chamber 32, thereby increasing the inlet pressure to or above the threshold value.

Upon determining that the inlet pressure is at least as great as the threshold value, the controller 18 commands the centrifugal separator 16 to rotate the centrifuge chamber 32 at a lower rate (step 122 of FIG. 17) in order to relieve the "air lock" condition and reduce the inlet pressure. In an exemplary embodiment, the rotational rate is reduced to the initial rotational rate (which is approximately 1,000 rpm in the illustrated embodiment). The controller 18 continues receiving signals from the pressure sensor A2 (step 124 of FIG. 17) and comparing them to the threshold value (step 126 of FIG. 17) until determining that the inlet pressure is again below the threshold value (i.e., that there are not air blocks at both the low-g outlet 74 and the high-g outlet 76), at which time the controller 18 returns to step 116 and again commands the centrifugal separator 16 to increase the rate at which the centrifuge chamber 32 is rotated (i.e., to a level that is greater than the initial rotational rate).

When the controller 18 determines (in step 120) that the inlet pressure is below the threshold value (i.e., that there are not air blocks at both the low-g outlet 74 and the high-g outlet 76), it advances to step 128 and considers signals received from the centrifugal separator sensor M1 to assess the nature of flow through lines L12 and L13 (the high- and low-g outlet conduits). On account of the centrifuge pump P3 and the low-g pump P4 operating at the same rate, there should be no blood flow through the high-g outlet conduit L12 (although blood will be present in the high-g outlet conduit L12), while blood should be flowing through the low-g conduit L13 at a constant rate. When the rate of blood flow through the high-g outlet conduit L12 increases and/or the rate of blood flow through the low-g outlet conduit L13 decreases, it is indicative of an air block B at the low-g outlet 74 (as shown in FIG. 20). Thus, in step 130, the controller 18 determines (based on signals received from the centrifugal separator sensor M1) whether blood is flowing though the high-g outlet conduit L12 and/or whether blood is flowing through the low-g outlet conduit L13 at a decreasing rate (which may include stagnant flow of blood through the low-g outlet conduit L13). This may be determined by the controller 18 according any suitable approach without departing from the scope of the present disclosure. For example, it is known that optical measurement of a stagnant liquid compared to a moving liquid through a conduit will produce a different optical output. This is particularly true for cell-based liquids, such as blood, due to the way in which cells line up in flow streamlines in moving liquid.

Upon determining that the rate of blood flow through the high-g outlet conduit L12 has increased and/or that the rate of blood flow through the low-g outlet conduit L13 has decreased (which may include being stagnant), the controller 18 commands the centrifugal separator 16 to rotate the centrifuge chamber 32 at a lower rate (step 132 of FIG. 17) in order to disperse the air block from the low-g outlet 74. In an exemplary embodiment, the rotational rate is reduced to the initial rotational rate (which is approximately 1,000 rpm in the illustrated embodiment). The controller 18 continues receiving signals from the centrifugal separator sensor M1 (step 134 of FIG. 17) and analyzing them (step 136 of FIG. 17) to determine whether the flow rates of blood through the high-g outlet conduit L12 and the low-g outlet conduit L13 are as expected (namely, with there being no blood flow through the high-g outlet conduit L12, while blood flows through the low-g outlet conduit L13 at a rate equal to the operational rate of the low-g pump P4). Upon determining that the flow rates of blood through the high-g outlet conduit L12 and the low-g outlet conduit L13 are as expected (i.e., that there is no air block at the low-g outlet 74), the controller 18 returns to step 116 and again commands the centrifugal separator 16 to increase the rate at which the centrifuge chamber 32 is rotated (i.e., to a level that is greater than the initial rotational rate).

The process of alternately increasing and decreasing the rate at which the centrifuge chamber 32 is rotated in response to signals from the pressure sensor A2 and the centrifugal separator sensor M1 continues until the signals indicate that (at an increased rotational rate) the inlet pressure is below the threshold value (as determined by the controller 18 at step 120 of FIG. 17) and that the flow rates of blood through the high-g outlet conduit L12 and the low-g outlet conduit L13 are as expected (as determined by the controller 18 at step 130 of FIG. 17). At this time, the controller 18 determines (at step 138 of FIG. 17) whether the current rotational rate is equal to the rotational rate required to separate the blood into its constituents (which rotational rate is approximately 4,500 rpm in the illustrated embodiment). If so, the controller 18 ends the priming procedure and begins blood separation (at step 140 of FIG. 17). Otherwise, if the current rotational rate is less than the rotational rate required to separate the blood into its constituents, the controller 18 will command the centrifugal separator 16 to continue increasing the rate at which the centrifuge chamber 32 is rotated (while continuing to assess the signals from the pressure sensor A2 and the centrifugal separator sensor M1 along the way, as at steps 116-138 of FIG. 17) until the required rotational rate has been reached and then ends the priming procedure (at step 140 of FIG. 17) and begins blood separation. Once all of the air has been removed from the centrifuge chamber 32, the rotational rate should be able to be quickly increased to the required rate, with a minimal volume of blood being used to prime the centrifuge chamber 32.

D. Other Embodiments

The preceding description is directed to a procedure in which a continuous-flow centrifuge chamber is primed using the fluid that is to be separated using the centrifuge chamber (i.e., blood being used to prime a centrifuge chamber 32, with the centrifuge chamber 32 subsequently being used to separate the blood). However, it should be understood that the priming approach described herein may be employed with a priming fluid that is different from the fluid that is to be separated using the centrifuge chamber. For example, in the case of a centrifuge chamber to be used to separate blood, saline or anticoagulant could instead be used as a priming fluid. Such a priming procedure would proceed as described above for a blood prime, with some notable differences. First, the blood source would not need to be connected to the fluid flow circuit 12 during the priming procedure, but could be elsewhere until priming has been completed. Further, rather than the source pump P2 operating at a higher rate than the centrifuge pump P3 (in order to direct some blood directly into the in-process bag F3), the two pumps P2 and P3 may be operated at the same rate, to direct all of the priming fluid into the centrifuge chamber 32.

In the case of anticoagulant being used as a priming fluid, flow through the fluid flow circuit 12 would be as shown in FIG. 16, except for the manual clamp 51 being closed and the anticoagulant pump P1 being operated at a higher rate that is equal to the rates of the source pump P2 and the centrifuge pump P3. The controller 18 would otherwise execute the priming procedure as shown in FIG. 17.

As for the case of saline being used as a priming fluid, flow through the fluid flow circuit 12 would be as shown in FIG. 16, except for the anticoagulant pump P1 being inactive, the valve V3 associated with valve station C3 being open, and the valve V10 associated with valve station C10 being closed. Such an arrangement causes the source pump P2 to draw saline from the saline bag F2 via line L23, with the saline being directed into the centrifuge chamber 32. The controller 18 otherwise executes the priming procedure as shown in FIG. 17.

In either case, after the centrifuge chamber 32 and the other portions of the fluid flow circuit 12 have been primed, the fluid source is connected to the fluid flow circuit 12, the manual clamp 51 is opened, and then separation may begin.

In view of the foregoing, it should be clear that the priming principles described herein are not limited to use with any particular separation procedure, any particular fluid to be separated, or any particular priming fluid to be used. Additionally, while one particularly configured centrifuge chamber 32 is shown and described in detail herein, it should be understood that the priming principles described herein are applicable to differently configured continuous-flow centrifuge chambers.

Aspects

Aspect 1. A fluid processing device, comprising: a controller; a centrifuge configured to receive and rotate a continuous-flow centrifuge chamber of a fluid flow circuit; a pump system configured to convey fluid through the fluid flow circuit; an optical detection assembly configured to monitor low- and high-g outlet conduits connected to the centrifuge chamber and to transmit signals to the controller that are indicative of the nature of flow through the low- and high-g outlet conduits; and a pressure sensor configured to measure an inlet pressure of fluid flowing into the centrifuge chamber and to transmit signals to the controller that are indicative of the inlet pressure, wherein the controller is configured to execute a priming procedure including controlling the centrifuge to rotate the centrifuge chamber at an initial rotational rate, controlling the pump system to convey a priming fluid into the centrifuge chamber so as to convey air out of the centrifuge chamber via the low-g outlet conduit, determining whether the priming fluid is flowing through the low-g outlet conduit and, upon determining that the priming fluid is flowing through the low-g outlet conduit, controlling the centrifuge to increase the rate at which the centrifuge chamber is rotated so as to move air remaining in the centrifuge chamber toward the low-g outlet conduit, determining whether, at the increased rotational rate, the inlet pressure is less than a threshold value, a flow rate of the priming fluid through the low-g outlet conduit is decreasing, and a flow rate of the priming fluid through the high-g outlet conduit is increasing, and upon determining that, at the increased rotational rate, the inlet pressure is less than the threshold value, the flow rate of the priming fluid through the low-g outlet conduit is not decreasing, and the flow rate of the priming fluid through the high-g outlet conduit is not increasing, ending the priming procedure.

Aspect 2. The fluid processing device of Aspect 1, wherein the pump system includes a centrifuge pump configured to convey fluid into the centrifuge chamber and a low-g pump configured to convey fluid out of the centrifuge chamber via the low-g outlet conduit, and the controller is further configured to, prior to determining whether the priming fluid is flowing through the low-g outlet conduit, control the low-g pump to operate at a first flow rate that is less than a flow rate at which the centrifuge pump is operating, determine whether the priming fluid is flowing through the high-g outlet conduit while the low-g pump is operating at the first flow rate, and upon determining that the priming fluid is flowing through the high-g outlet conduit while the low-g pump is operating at the first flow rate, control the low-g pump to operate at a second flow rate that is greater than the first flow rate.

Aspect 3. The fluid processing device of Aspect 2, wherein the second flow rate is equal to the flow rate at which the centrifuge pump is operating.

Aspect 4. The fluid processing device of Aspect 3, wherein the controller is further configured to decrease the flow rates of the low-g pump and the centrifuge pump after determining that the priming fluid is flowing through the low-g outlet conduit.

Aspect 5. The fluid processing device of any one of the preceding Aspects, wherein the controller is further configured to, upon determining that the inlet pressure is greater or equal than the threshold value at the increased rotational rate, control the centrifuge to decrease the rate at which the centrifuge chamber is rotated, and upon determining that the inlet pressure is less than the threshold value at the decreased rotational rate, again control the centrifuge to increase the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

Aspect 6. The fluid processing device of Aspect 5, wherein the controller is further configured to decrease the rotational rate to the initial rotational rate upon determining that the inlet pressure is greater or equal than the threshold value at the increased rotational rate.

Aspect 7. The fluid processing device of any one of the preceding Aspects, wherein the controller is further configured to, upon determining that the inlet pressure is less than the threshold value at the increased rotational rate, but that the flow rate of the priming fluid through the low-g outlet conduit is decreasing and/or the flow rate of the priming fluid through the high-g outlet conduit is increasing, control the centrifuge to decrease the rate at which the centrifuge chamber is rotated, and upon determining that the flow rate of the priming fluid through the low-g outlet conduit is not decreasing and/or the flow rate of the priming fluid through the high-g outlet conduit is not increasing at the decreased rotational rate, again control the centrifuge to increase the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

Aspect 8. The fluid processing device of Aspect 7, wherein the controller is further configured to decrease the rotational rate to the initial rotational rate upon determining that the flow rate of the priming fluid through the low-g outlet conduit is decreasing and/or the flow rate of the priming fluid through the high-g outlet conduit is increasing at the increased rotational rate.

Aspect 9. The fluid processing device of any one of the preceding Aspects, wherein the controller is further configured to execute a fluid separation procedure after ending the priming procedure, and the priming fluid is the fluid to be separated during the fluid separation procedure.

Aspect 10. The fluid processing device of any one of Aspects 1-8, wherein the controller is further configured to execute a fluid separation procedure after ending the priming procedure, and the priming fluid is not the fluid to be separated during the fluid separation procedure.

Aspect 11. A method of priming a continuous-flow centrifuge chamber, comprising: rotating the centrifuge chamber at an initial rotational rate; conveying a priming fluid into the centrifuge chamber so as to convey air out of the centrifuge chamber via a low-g outlet conduit connected to the centrifuge chamber; determining whether the priming fluid is flowing through the low-g outlet conduit and, upon determining that the priming fluid is flowing through the low-g outlet conduit, increasing the rate at which the centrifuge chamber is rotated so as to move air remaining in the centrifuge chamber toward the low-g outlet conduit; determining whether, at the increased rotational rate, an inlet pressure of the priming fluid flowing into the centrifuge chamber is less than a threshold value, a flow rate of the priming fluid through the low-g outlet conduit is decreasing, and a flow rate of the priming fluid through a high-g outlet conduit connected to the centrifuge chamber is increasing, and upon determining that, at the increased rotational rate, the inlet pressure is less than the threshold value, the flow rate of the priming fluid through the low-g outlet conduit is not decreasing, and the How rate of the priming fluid through the high-g outlet conduit is not increasing, ending the priming procedure.

Aspect 12. The method of Aspect 11, wherein said conveying the priming fluid into the centrifuge chamber includes operating a centrifuge pump to convey the fluid into the centrifuge chamber and operating a low-g pump to convey the priming fluid out of the centrifuge chamber via the low-g outlet conduit, with the low-g pump operating at a first flow rate that is less than a flow rate at which the centrifuge pump is operating, determining whether the priming fluid is flowing through the high-g outlet conduit while the low-g pump is operating at the first flow rate, and upon determining that the priming fluid is flowing through the high-g outlet conduit while the low-g pump is operating at the first flow rate, controlling the low-g pump to operate at a second flow rate that is greater than the first flow rate.

Aspect 13. The method of Aspect 12, wherein the second flow rate is equal to the flow rate at which the centrifuge pump is operating.

Aspect 14. The method of Aspect 18, further comprising decreasing the flow rates of the low-g pump and the centrifuge pump after determining that the priming fluid is flowing through the low-g outlet conduit.

Aspect 15. The method of any one of Aspects 11-14, further comprising, upon determining that the inlet pressure is greater or equal than the threshold value at the increased rotational rate, decreasing the rate at which the centrifuge chamber is rotated, and upon determining that the inlet pressure is less than the threshold value at the decreased rotational rate, again increasing the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

Aspect 16. The method of Aspect 15, further comprising decreasing the rotational rate to the initial rotational rate upon determining that the inlet pressure is greater or equal than the threshold value at the increased rotational rate.

Aspect 17. The method of any one of Aspects 11-16, further comprising, upon determining that the inlet pressure is less than the threshold value at the increased rotational rate, but that the flow rate of the priming fluid through the low-g outlet conduit is decreasing and/or the flow rate of the priming fluid through the high-g outlet conduit is increasing, decreasing the rate at which the centrifuge chamber is rotated, and upon determining that the flow rate of the priming fluid through the low-g outlet conduit is not decreasing and/or the flow rate of the priming fluid through the high-g outlet conduit is not increasing at the decreased rotational rate, again increasing the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

Aspect 18. The method of Aspect 17, further comprising decreasing the rotational rate to the initial rotational rate upon determining that the flow rate of the priming fluid through the low-g outlet conduit is decreasing and/or the flow rate of the priming fluid through the high-g outlet conduit is increasing at the increased rotational rate.

Aspect 19. The method of any one of Aspects 11-18, wherein the priming fluid is a fluid to be separated using the centrifuge chamber after ending the priming procedure.

Aspect 20. The method of any one of Aspects 11-18, wherein the priming fluid is not a fluid to be separated using the centrifuge chamber after ending the priming procedure.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:
1. A fluid processing device, comprising:
a controller;
a centrifuge configured to receive and rotate a continuous-flow centrifuge chamber of a fluid flow circuit;
a pump system configured to convey fluid through the fluid flow circuit;
an optical detection assembly configured to monitor low- and high-g outlet conduits connected to the centrifuge chamber and to transmit signals to the controller that are indicative of the nature of flow through the low- and high-g outlet conduits; and
a pressure sensor configured to measure an inlet pressure of fluid flowing into the centrifuge chamber and to transmit signals to the controller that are indicative of the inlet pressure, wherein the controller is configured to execute a priming procedure including
controlling the centrifuge to rotate the centrifuge chamber at an initial rotational rate,
controlling the pump system to convey a priming fluid into the centrifuge chamber so as to convey air out of the centrifuge chamber via the low-g outlet conduit,
determining whether the priming fluid is flowing through the low-g outlet conduit and, upon determining that the priming fluid is flowing through the low-g outlet conduit, controlling the centrifuge to increase the rate at which the centrifuge chamber is rotated so as to move air remaining in the centrifuge chamber toward the low-g outlet conduit,
determining whether, at the increased rotational rate, the inlet pressure is less than a threshold value, a flow rate of the priming fluid through the low-g outlet conduit is decreasing, and a flow rate of the priming fluid through the high-g outlet conduit is increasing, and
upon determining that, at the increased rotational rate, the inlet pressure is less than the threshold value, the flow rate of the priming fluid through the low-g outlet conduit is not decreasing, and the flow rate of the priming fluid through the high-g outlet conduit is not increasing, ending the priming procedure.

2. The fluid processing device of claim 1, wherein
the pump system includes a centrifuge pump configured to convey fluid into the centrifuge chamber and a low-g pump configured to convey fluid out of the centrifuge chamber via the low-g outlet conduit, and
the controller is further configured to, prior to determining whether the priming fluid is flowing through the low-g outlet conduit,
control the low-g pump to operate at a first flow rate that is less than a flow rate at which the centrifuge pump is operating,
determine whether the priming fluid is flowing through the high-g outlet conduit while the low-g pump is operating at the first flow rate, and
upon determining that the priming fluid is flowing through the high-g outlet conduit while the low-g pump is operating at the first flow rate, control the low-g pump to operate at a second flow rate that is greater than the first flow rate.

3. The fluid processing device of claim 2, wherein the second flow rate is equal to the flow rate at which the centrifuge pump is operating.

4. The fluid processing device of claim 3, wherein the controller is further configured to decrease the flow rates of the low-g pump and the centrifuge pump after determining that the priming fluid is flowing through the low-g outlet conduit.

5. The fluid processing device of claim 1, wherein the controller is further configured to, upon determining that the inlet pressure is greater or equal than the threshold value at the increased rotational rate,
control the centrifuge to decrease the rate at which the centrifuge chamber is rotated, and
upon determining that the inlet pressure is less than the threshold value at the decreased rotational rate, again control the centrifuge to increase the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

6. The fluid processing device of claim 5, wherein the controller is further configured to decrease the rotational rate to the initial rotational rate upon determining that the inlet pressure is greater or equal than the threshold value at the increased rotational rate.

7. The fluid processing device of claim 1, wherein the controller is further configured to, upon determining that the inlet pressure is less than the threshold value at the increased rotational rate, but that the flow rate of the priming fluid through the low-g outlet conduit is decreasing and/or the flow rate of the priming fluid through the high-g outlet conduit is increasing,
control the centrifuge to decrease the rate at which the centrifuge chamber is rotated, and
upon determining that the flow rate of the priming fluid through the low-g outlet conduit is not decreasing and/or the flow rate of the priming fluid through the high-g outlet conduit is not increasing at the decreased rotational rate, again control the centrifuge to increase the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

8. The fluid processing device of claim 7, wherein the controller is further configured to decrease the rotational rate to the initial rotational rate upon determining that the flow rate of the priming fluid through the low-g outlet conduit is decreasing and/or the flow rate of the priming fluid through the high-g outlet conduit is increasing at the increased rotational rate.

9. The fluid processing device of claim 1, wherein
the controller is further configured to execute a fluid separation procedure after ending the priming procedure, and
the priming fluid is the fluid to be separated during the fluid separation procedure.

10. The fluid processing device of claim 1, wherein
the controller is further configured to execute a fluid separation procedure after ending the priming procedure, and
the priming fluid is not the fluid to be separated during the fluid separation procedure.

11. A method of priming a continuous-flow centrifuge chamber, comprising:
rotating the centrifuge chamber at an initial rotational rate;
conveying a priming fluid into the centrifuge chamber so as to convey air out of the centrifuge chamber via a low-g outlet conduit connected to the centrifuge chamber;
determining whether the priming fluid is flowing through the low-g outlet conduit and, upon determining that the priming fluid is flowing through the low-g outlet conduit, increasing the rate at which the centrifuge chamber is rotated so as to move air remaining in the centrifuge chamber toward the low-g outlet conduit;
determining whether, at the increased rotational rate, an inlet pressure of the priming fluid flowing into the centrifuge chamber is less than a threshold value, a flow rate of the priming fluid through the low-g outlet conduit is decreasing, and a flow rate of the priming fluid through a high-g outlet conduit connected to the centrifuge chamber is increasing, and
upon determining that, at the increased rotational rate, the inlet pressure is less than the threshold value, the flow rate of the priming fluid through the low-g outlet conduit is not decreasing, and the flow rate of the priming fluid through the high-g outlet conduit is not increasing, ending the priming procedure.

12. The method of claim 11, wherein said conveying the priming fluid into the centrifuge chamber includes
operating a centrifuge pump to convey the fluid into the centrifuge chamber and operating a low-g pump to convey the priming fluid out of the centrifuge chamber via the low-g outlet conduit, with the low-g pump operating at a first flow rate that is less than a flow rate at which the centrifuge pump is operating,
determining whether the priming fluid is flowing through the high-g outlet conduit while the low-g pump is operating at the first flow rate, and
upon determining that the priming fluid is flowing through the high-g outlet conduit while the low-g pump is operating at the first flow rate, controlling the low-g pump to operate at a second flow rate that is greater than the first flow rate.

13. The method of claim 12, wherein the second flow rate is equal to the flow rate at which the centrifuge pump is operating.

14. The method of claim 13, further comprising decreasing the flow rates of the low-g pump and the centrifuge pump after determining that the priming fluid is flowing through the low-g outlet conduit.

15. The method of claim 11, further comprising, upon determining that the inlet pressure is greater or equal than the threshold value at the increased rotational rate,
   decreasing the rate at which the centrifuge chamber is rotated, and
   upon determining that the inlet pressure is less than the threshold value at the decreased rotational rate, again increasing the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

16. The method of claim 15, further comprising decreasing the rotational rate to the initial rotational rate upon determining that the inlet pressure is greater or equal than the threshold value at the increased rotational rate.

17. The method of claim 11, further comprising, upon determining that the inlet pressure is less than the threshold value at the increased rotational rate, but that the flow rate of the priming fluid through the low-g outlet conduit is decreasing and/or the flow rate of the priming fluid through the high-g outlet conduit is increasing,
   decreasing the rate at which the centrifuge chamber is rotated, and
   upon determining that the flow rate of the priming fluid through the low-g outlet conduit is not decreasing and/or the flow rate of the priming fluid through the high-g outlet conduit is not increasing at the decreased rotational rate, again increasing the rate at which the centrifuge chamber is rotated and again determine whether, at the increased rotational rate, the inlet pressure is less than the threshold value, the flow rate of the priming fluid through the low-g outlet conduit is decreasing, and the flow rate of the priming fluid through the high-g outlet conduit is increasing.

18. The method of claim 17, further comprising decreasing the rotational rate to the initial rotational rate upon determining that the flow rate of the priming fluid through the low-g outlet conduit is decreasing and/or the flow rate of the priming fluid through the high-g outlet conduit is increasing at the increased rotational rate.

19. The method of claim 11, wherein the priming fluid is a fluid to be separated using the centrifuge chamber after ending the priming procedure.

20. The method of claim 11, wherein the priming fluid is not a fluid to be separated using the centrifuge chamber after ending the priming procedure.

* * * * *